United States Patent
Wang et al.

(10) Patent No.: US 11,039,747 B2
(45) Date of Patent: Jun. 22, 2021

(54) SIGNAL OBTAINING METHOD AND SYSTEM

(71) Applicant: VITA-COURSE TECHNOLOGIES CO., LTD., Guangdong (CN)

(72) Inventors: Zhiyong Wang, Guangdong (CN); Liang Li, Guangdong (CN); Jiao Yu, Guangdong (CN)

(73) Assignee: VITA-COURSE TECHNOLOGIES CO., LTD., Shenzhen (CN)

( * ) Notice: Subject to any disclaimer, the term of this patent is extended or adjusted under 35 U.S.C. 154(b) by 364 days.

(21) Appl. No.: 15/576,846

(22) PCT Filed: May 27, 2015

(86) PCT No.: PCT/CN2015/079956
§ 371 (c)(1),
(2) Date: Nov. 26, 2017

(87) PCT Pub. No.: WO2016/187847
PCT Pub. Date: Dec. 1, 2016

(65) Prior Publication Data
US 2018/0160905 A1    Jun. 14, 2018

(51) Int. Cl.
*A61B 5/024*    (2006.01)
*A61B 5/00*    (2006.01)

(52) U.S. Cl.
CPC .......... *A61B 5/0004* (2013.01); *A61B 5/0017* (2013.01); *A61B 5/0051* (2013.01); *A61B 5/02416* (2013.01); *A61B 5/7203* (2013.01); *A61B 5/7246* (2013.01); *A61B 5/7264* (2013.01); *A61B 2562/0223* (2013.01);
(Continued)

(58) Field of Classification Search
CPC ............ A61B 5/02433; A61B 5/02416; A61B 5/1455
See application file for complete search history.

(56) References Cited

U.S. PATENT DOCUMENTS 5,431,170 A * 7/1995 Mathews ............. A61B 5/0002
600/323
5,853,364 A    12/1998 Baker, Jr. et al.
6,997,879 B1    2/2006 Turcott
(Continued)

FOREIGN PATENT DOCUMENTS

CN    2824836 Y    10/2006
CN    101099677 A    1/2008
(Continued)

OTHER PUBLICATIONS

International Search Report for PCT/CN2015/079956 dated May 27, 2015, 2 pages.
(Continued)

*Primary Examiner* — Puya Agahi
(74) *Attorney, Agent, or Firm* — Metis IP LLC

(57) ABSTRACT

The present invention provides a signal obtaining method and system, which includes functions of signal collection, analysis, calculation and output. The system can be configured to obtain vital signs by: collecting two or more physiological signals, calculating relation information between the two or more physiological signals, obtaining the vital signs by calculation based on the relation information, and output the obtained vital signs.

18 Claims, 7 Drawing Sheets

(52) U.S. Cl.
CPC .......... *A61B 2562/0233* (2013.01); *A61B 2562/0271* (2013.01)

(56) References Cited

U.S. PATENT DOCUMENTS

| | | |
|---|---|---|
| 7,738,935 B1 | 6/2010 | Turcott |
| 8,463,349 B2 | 6/2013 | Diab et al. |
| 2005/0038327 A1* | 2/2005 | Tanaka .......... A61B 5/1118 600/301 |
| 2007/0167844 A1 | 7/2007 | Asada et al. |
| 2011/0054336 A1 | 3/2011 | Jornod |
| 2014/0073957 A1* | 3/2014 | Rodriguez-Llorente .......... A61B 5/7214 600/479 |
| 2014/0213863 A1* | 7/2014 | Loseu .......... A61B 5/7207 600/324 |
| 2014/0243648 A1 | 8/2014 | Dubielczyk |
| 2015/0046095 A1 | 2/2015 | Takahashi et al. |
| 2015/0305684 A1 | 10/2015 | Gross |
| 2017/0112398 A1* | 4/2017 | Narusawa .......... A61B 5/02416 |

FOREIGN PATENT DOCUMENTS

| | | |
|---|---|---|
| CN | 103860152 A | 6/2014 |
| CN | 104224144 A | 12/2014 |
| CN | 104586370 A | 5/2015 |
| WO | 0115597 A1 | 3/2001 |
| WO | 2014091382 A1 | 6/2014 |

OTHER PUBLICATIONS

International Search Report in PCT/CN2015/079956 dated Mar. 2, 2016, 6 pages.
Written Opinion in PCT/CN2015/079956 dated Mar. 2, 2016, 8 pages.

* cited by examiner

US 11,039,747 B2

SIGNAL OBTAINING METHOD AND SYSTEM

PRIORITY DOCUMENT

This application is a U.S. national stage application under 35 U.S.C. § 371 of International Application No. PCT/CN2015/079956, filed on May 27, 2015, designating the United States of America, the contents of which are hereby incorporated by reference in their entirety.

TECHNICAL FIELD

The present invention relates to a signal obtaining method and system, and more particularly, to a signal obtaining method and system when a living organism or an object is under movement/vibration.

BACKGROUND

Signal detection, signal control, signal calibration and signal processing are all very common and important whether in the medical treatment, industrial control, automation control, aerospace, automotive transportation, mobile communication, household appliance and other fields. In particular, the precise extraction and process of low-frequency and small-amplitude signals are directly or indirectly related to the failure-free operation of various industrial processes.

In the field of medical treatment, the precise extraction of physiological signals may directly or indirectly affect measurement of various vital signs. A living organism may generate and release a large number of physiological signals at all times. The physiological signals may be summarized in two broad categories: chemical information (information related to chemical compositions of a living organism and changes thereof) and physical information (information related to a shape, a position and a relative relationship of organs of a living organism, force generated by exercise, heat, sound and light). A large number of physiological signals are directly or indirectly related to vital signs of a living organism, and the physiological signals may directly or indirectly reflect the vital signs of a living organism.

During the process of using a photoelectric sensor to collect and detect physiological signals of a living organism, vibration or movement of a light source or an information-to-collect object may cause great interference(s) or noise(s) to the result of information collection, resulting in distortion or inundation of the signals. For example, Photoplethysmograph (referred to as PPG) is a method of non-invasive detection of changes in the volume of blood in a living organism using a photoelectric means. By measuring PPG signals, vital signs such as blood pressure of the living organism may be further calculated and obtained. The photoelectric pulse wave (i.e., a PPG signal) belongs to a low-frequency physiological signal, and most of the movement/vibration frequency caused by the movement of the living organism during the movement of the living organism also happens to lie within the same frequency range. Due to the similarity of the two frequencies, conventional hardware filtering or software filtering cannot achieve a good denoising effect. Therefore, a better method and system for removing movement caused noises is needed.

SUMMARY

The present disclosure discloses a method, comprising: transmitting a beam of light to an object; collecting a first signal reflected by the object; collecting a second signal reflected by the object, wherein the second signal is different from the first signal; calculating and extracting relation information between the first signal and the second signal; calculating and obtaining a feature relating to the object using the relation information.

According to an embodiment of the present application, a spectrum of the beam of light is at least one of the spectrums of a visible light, an infrared light, or a far-infrared light.

According to an embodiment of the present application, the object is a living organism, and the first signal comprises a PPG signal relating to the living organism and a moving/vibrating signal relating to the living organism.

According to an embodiment of the present application, the object is a living organism, and the second signal comprises a moving/vibrating signal of the living organism.

According to an embodiment of the present application, the calculating and extracting relation information further comprises processing of normalization.

According to an embodiment of the present application, the calculating and extracting relation information further comprises setting a correlation coefficient.

According to an embodiment of the present application, the object is a living organism, and the correlation coefficient comprises a PPG signal relating to the living organism.

The present disclosure also discloses a system, comprising: a transmitter, configured to transmit a beam of light to an object; a first receiver, configured to receive a first signal reflected by the object;

a second receiver, configured to receive a second signal reflected by the object, the second signal being different from the first signal; an analysis module, configured to calculate relation information between the first signal and the second signal; and a calculation module, configured to calculate and obtain a feature relating to the object based on the relation information.

According to an embodiment of the present application, a spectrum of the beam of light is at least one of the spectrums of a visible light, an infrared light, or a far-infrared light.

According to an embodiment of the present application, at least one parameter on resistance, current, voltage or sensitivity of light intensity of the first receiver is different from that of the second receiver.

According to an embodiment of the present application, the object is a living organism, and the first signal comprises a PPG signal relating to the living organism and a moving/vibrating signal relating to the living organism.

According to an embodiment of the present application, the object is a living organism, and the second signal comprises a moving/vibrating signal of the living organism.

According to an embodiment of the present application, the analysis module performs processing of normalization on the first signal or the second signal.

According to an embodiment of the present application, the analysis module is capable of selecting correlation coefficients, and capable of selecting a corresponding correlation coefficient when calculating the relation information.

According to an embodiment of the present application, the object is a living organism, and the correlation coefficient comprises a PPG signal relating to the living organism.

According to an embodiment of the present application, the system further comprises an output module that comprises a displaying device.

DETAILED DESCRIPTION

Figure 1:
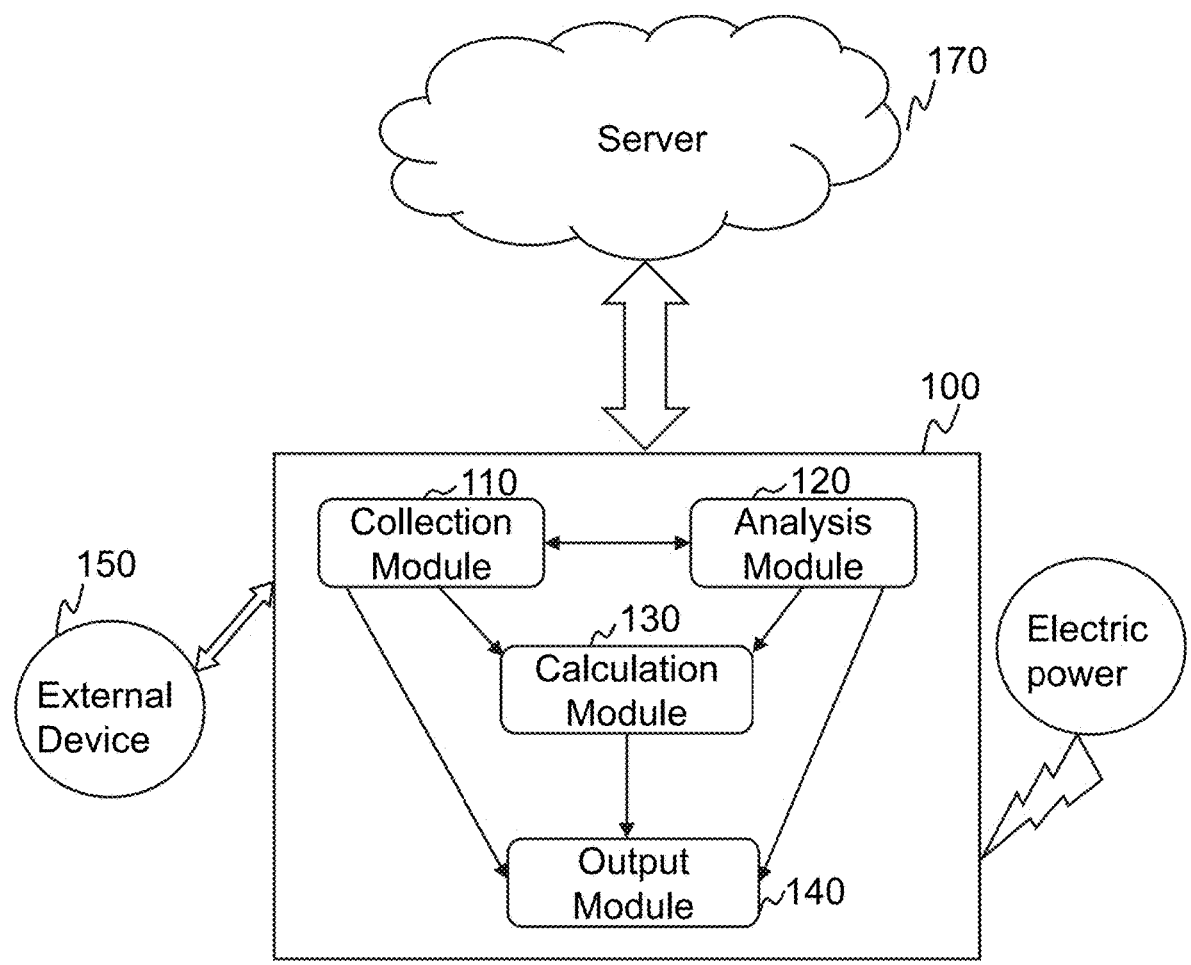
FIG. 1 is a schematic diagram of a system.

The signal obtaining method and system related to the present description may be applied to various fields, including but not limited to fields of medical treatment, industrial control, automation, aerospace, automotive transportation, mobile communication, household appliance control, etc. In particular, the system may be applied to the medical treatment field as a system for obtaining vital signs. The present invention may be applied to the above-mentioned fields for signal detection, signal control, signal calibration, signal processing or the like, so as to implement precise signal detection, signal control and signal extraction. In particular, the detection and extraction of low-frequency and small-amplitude signal is performed with high accuracy and low amount of calculation. For example, flow signals of liquid in an engine cylinder, flow signals of liquid in a pipe, movement of objects on or near a solid surface of movement/vibration, relative movement between two solid surfaces, and the like. In particular, the present invention may be used to collect physiological signals and/or obtain vital signs of a living organism, or the like. The present description will describe a vital sign obtaining system in the medical treatment field as an example, but the whole method and process are equally applicable to other fields.

When used as a vital sign obtaining system, the present invention may be applied to a variety of situations, including but not limited to guardianship (including but not limited to guardianship of the elderly, guardianship of middle-aged persons, guardianship of young people and guardianship of young children), medical diagnosis (including but not limited to electrocardiogram diagnosis, pulse diagnosis, blood pressure diagnosis, blood oxygen diagnosis), movement monitoring (including but not limited to long-distance running, dash, sprint, cycling, rowing, archery, horseback riding, swimming and climbing), hospital nursing (including but not limited to critically ill patient monitoring, genetic disease patient monitoring and emergency patient monitoring), pet care (critically ill pet care, newborn pet care and home pet care) or the like.

The present invention relates to a vital sign obtaining system which can be used to collect and obtain, from a living organism, one or more vital signs, for example, physical and chemical information such as electrocardiogram, a pulse, a blood pressure, blood oxygen, a cardiac rate, a body temperature, HRV, BPV, brain waves, ultra-low frequency waves emitted by a human body, respiration, a musculoskeletal state, blood sugar, blood lipids, a blood concentration, a platelet content, a height, and a weight. The vital sign obtaining system may include a collection module, an analysis module, a calculation module, an output module, etc. The collection module may be used to collect two or more signals related to the living organism. The analysis module may be used to analyze features of two or more signals and extract relation information between the signals. In the two or more collected signals related to the living organism, at least one of the signals may be a physiological signal including noises, and at least one of the signals may be a noise signal mainly including noises. The system (e.g., the analysis module in the system) may use the noise signal mainly including noises to modify the collected physiological signal including noises. The calculation module may calculate and obtain vital signs using the relation information. The output module may be used to output the vital signs. The system may remove the noise interfering signal in signals of the living organism well, and the calculated amount thereof is small and the result is accurate. For example, the system may remove a movement/vibration noise interfering signal in a PPG signal of the living organism well. The system may monitor vital signs of living organisms. The monitoring may be continuous, and the monitoring may also be discontinuous. For example, the monitoring may be periodic or triggered by an instruction or a signal. The instruction or signal may be an instruction input by a user (such as a patient and medical care personnel). The instruction or signal may also be a signal, for example, a signal related to the monitored living organism. For example, the signal related to the monitored living organism is a PPG signal, the monitoring thereof may be triggered by a related signal (such as heartbeat) exceeding a threshold. The monitoring may be real-time, and may also be non-real-time. For example, one or more physiological signals of a living organism in a certain time period may be temporarily stored, and the calculation module may calculate an average or near-average vital sign of the living organism within the time period. The vital sign obtaining system may output monitored vital sign status of the living organism in real time (or non-real time), such as electrocardiogram, pulse, blood pressure, blood oxygen concentration, cardiac rate variability, blood concentration, blood lipids and other information. The system may transmit a monitored result to an external device (including but not limited to a storage device, a display device or a server). The system may remotely provide the vital signs to relevant third parties, such as hospitals, nursing facilities or related people. All of the signals or vital signs described above may be transmitted in a wired or wireless manner.

In order to make the technical scheme of the embodiment of the present invention more clearly, drawings need to be used in the description of the embodiments will be briefly introduced. It is obvious that drawings in the following description are only some embodiments of the present application, and the present invention may be applied to the other similar scenario according to these drawings by those skilled in the art without paying creative efforts. Unless it is obvious in the language environment or otherwise indicated, the same reference numerals represent the same structure or operation.

In the present application and claims, the words "a/an", "one", "a kind of" and/or "the" are not specifically singular, and may include plural numbers unless the context clearly indicates otherwise. In general, the terms "include" and "comprise" may only indicate that explicitly identified steps and elements are included, but such steps and elements do not constitute an exclusive list, and a method or device may also include other steps or elements.

FIG. 1 shows a schematic diagram of a system that can obtain vital signs. The system may include, but is not limited to, one or more engines 100, one or more external devices 150, one or more electric powers 160 and/or a server 170. The engine 100 may include, but is not limited to, a collection module 110, an analysis module 120, a calculation module 130 and an output module 140. The collection module 110 may be configured to collect, receive and obtain one or more signals. The module may collect a signal through photoelectric sensing, temperature sensing, humidity variation, pressure variation, body surface potential variation, voltage variation, current variation or magnetic field variation, and may be connected to other external devices so as to obtain a signal through manual input. The collection module may obtain acoustic, optical, magnetic, thermal, mechanical and other types of signals. The collected signal types may include, but are not limited to, one or more of physiological signals such as pulse waves, electrocardiogram, a cardiac rate, a blood pressure, blood oxygen, respiration, a height, a weight, a body temperature, a musculoskeletal state, brain waves, a fat content, a blood sugar concentration, a blood concentration and blood flow, and non-physiological signals such as a vital moving/vibrating signal of a living organism. The collection module 110 may not only obtain static signals but also obtain dynamic signals. For example, the collection module 110 may obtain a PPG signal of a living organism through photoelectric sensing, and may also obtain a PPG signal and a moving/vibrating signal of the living organism when the living organism is in movement or vibration. The collection module 110 may collect two or more signals at the same time or time sharing. The module may include one or more signal collection units. For example, the module may include one or more light source transmitters and one or more photoelectric sensor receivers. The plurality of light source transmitters may transmit a plurality of beams of light with different features such as but not limited to infrared light and green light, red light and green light, infrared light and red light. The plurality of beams of light may be in the same phase or in different phases; may have different wavelengths or the same wavelength; may be in different frequency bands or the same frequency band; and may have the same intensity or different intensities. In particular, the plurality of beams of light may also be obtained by adding the same or different carrier signals to one or more original beams of light/signals and performing modulation. For example, spectrums of the original beams of light/signals may be moved to any spectral range through frequency modulation, phase modulation, amplitude modulation, etc., which facilitates the beam of light/signal transmission. When two or more signals are collected, the plurality of sensor receivers may receive the plurality of signals at the same time. A certain sampling frequency may be set to receive the plurality of signals time sharing, and a sampling period may be set for cyclic sampling. It should be noted that the transmitter and the receiver are not necessarily included in the collection module 110. The transmitter and receiver may be included in other modules separately; may be included in other modules together; and one of which may be included in the collection module and the other may be included in other modules. The light source transmitters and the photoelectric sensor receivers may be arranged and combined in any form, and two or more same or different signals may be collected. The collection module 110 may make full use of various devices that may already exist and may come into the future. The devices may be a blood pressure measuring device such as a wrist-watch sphygmomanometer, a wrist sphygmomanometer, or an upper arm sphygmomanometer; may be an electrocardiogram monitoring device such as an electrocardiogram monitoring system of an electrocardiogram monitor; and may also be a pulse wave detector, a brain wave monitor, a respiration detector, a blood measuring device, etc. The device used by the collection module 110 may be local or remote, may be a large-scale medical device, or a smart wearable device such as a watch, a bracelet, a neck ring, eyeglasses and an earphone. It should be noted that the above-mentioned instruments or devices may be a part of the collection module 110, or a separate module included in the system independently; and may also be an external device independent of the system from which the collection module may read signals. The instruments or devices are not necessary for implementing functions of the system.

The collection module 110 may be integrated with a calibration unit or a compensation unit (not shown), or the engine 100 may be provided with a separate calibration unit or a compensation unit (not shown) for adjusting, optimizing, calibrating the two or more collected signals or removing irrelevant error interference. The signal collection may be affected by a variety of factors. The factors may affect one or more of the features of the signal such as a waveform, a wave crest, a wave trough, peak amplitude, peak point spacing, a phase, a frequency, and a period. For example, physiological signals of one living organism at different times of one day may have a certain difference. Physiological signals of one living organism in different psychological or physiological state may also have differences. Similarly, physiological signals of different living organisms in the same psychological/physiological state or at the same time may also have differences. The irrelevant effects or interference may be removed, attenuated, or compensated by setting a calibration unit (not shown) or a compensation unit (not shown). The collection module 110 may be integrated with a corresponding calibration unit (not shown) or a compensation unit (not shown), or the engine 100 may be provided with a corresponding separate calibration unit (not shown) or compensation unit (not shown) so as to adjust, optimize, calibrate the signal or remove the error interference, so that the accuracy of obtained physiological signals of a living organism is increased. In addition, the collection module 110 may be integrated with a corresponding adaptive unit (not shown). The adaptive unit may adjust different parameter states for different living organisms. The adaptive unit may store physiological signals collected, received and obtained from the same living organism into the server 170 (e.g., a cloud server), so that the collection module 110 may have an adaptive function. For example, the collection module 110 may storage data collected every time to the server 170 (e.g., a cloud server) and mark different data of different living organisms accordingly. The module may start a machine learning process according to data of the same living organism at different times or different states and make corresponding adjustments to the collected signals or data according to different features of different living organisms. The adaptive function may enable the server 170 to form an individual physiological signal database of the same living organism so as to make the collected physiological signals of the living organism more accurate. In addition, the photoelectric sensing may be affected by factors such as light intensity, skin color, skin roughness, skin temperature, skin humidity, environment temperature, and environment humidity. Therefore, the collection module 110 may be integrated with a corresponding environment adaptation unit (not shown), or an environment adaptation unit (not shown) included in the engine 100 may be connected with the collection module 110. For example, a modification or compensation unit corresponding to the environmental factors may be configured to compensate, modify, offset or remove the effects or interference of the environmental factors on the physiological signal features of the living organism. The above modification, deformation or variation of the system for analyzing vital signs should be within the protection scope of the present invention.

The analysis module 120 may be configured to perform various operations such as analysis, calculation and process on the collected signals. The analysis module 120 may be centralized or distributed. The analysis module 120 may perform operations such as analysis, computation and process on the signals. The processes may be real-time, and may also be non-real-time. The processes of analysis, calculation or processing may include, but are not limited to, various common feature analysis, statistical analysis, mathematical calculation and data processing. The processes of analysis, calculation or processing may be a direct mathematical operation, also may be based on software programming analysis. Data or analysis results, calculation results and processing results related in the processes of analysis, calculation or processing may be displayed in a waveform graphic form or in a digital form, but the display may not be essential. The various processes in the analysis module 120 described above are not necessary and are not limited to the sequential steps listed above. It will be apparent to those skilled in the art that various modifications and variations can be made in the form and details of the modules after understanding the contents and principles of the present invention without departing from the principles and the structures of the present invention. The processes may be arranged in any combination and the processes may be added or subtracted as needed, and these modifications and changes are still within the scope of the claims of the present invention. For example, in the processes of analysis or calculation, the same analysis method or calculation method may be used, or two or more analysis methods or calculation methods may be used simultaneously. For example, two or more analysis methods or calculation methods may be used for the same signal, and a plurality of results may be averaged by comparing analysis results or calculation results of different methods; or one of the analysis results or calculation results may be taken as a reference to verify rationality of other analysis or calculation results. Not all steps of analysis, calculation and processing are essential, and one or more steps may be deleted if necessary. A cache step may be added between any two processes in the processes of analysis, calculation, and processing, so as to store real-time or non-real-time data related in an operational process of the analysis module 120.

The calculation module 130 may be configured to calculate vital signs of a living organism based on physiological signals collected by the collection module 110 or analyzed by the analysis module 120. The calculation process may be real-time, and may also be non-real-time. The types of vital signs that may be calculated by the calculation module 130 may include, but are not limited to, one or more of vital signs such as a blood pressure, a pulse rate (PR), blood oxygen saturation, cardiac rate variability, heart murmur, bowel sounds, a pH value, a creatinine content, a transferase content, a body temperature and a carcinoembryonic antigen content. The calculation methods may include, but are not limited to, various mathematical calculation, statistical analysis, data processing or the like. The environment and other factors may be further considered in the calculation process, and a related calibration factor may be added. For example, a temperature coefficient, a humidity coefficient, an air flow coefficient, a barometric coefficient, a light coefficient, a time coefficient, a coefficient of a physiological or psychological state of a living organism, an age coefficient, or the like, or any combination thereof. The types of data or signals related in the calculation process may include, but are not limited to, the measurement of one or more physiological parameters of a living organism. For example, but not limited to, a height, a weight, a vital capacity, heartbeat parameters, a blood sugar content, measurement of blood viscosity, a diastolic blood pressure, a systolic blood pressure, measurement of a blood flow parameter, a PPG signal wave crest and wave trough, an ECG signal wave crest and wave trough, a pulse rate, a cardiac rate, a blood lipid content, a vascular tone, a skin tone, a brain wave frequency, gastrointestinal motility, liver and gallbladder morphology, a gastrointestinal mucosal parameter, an antibody content, and an enzyme content. The variety of calculation methods or calculation processes may be interconnected, or may be independent. There may be a direct relationship, also may be an indirect relationship. The calculation methods or calculation processes may exist in parallel or in series with each other. The data related in the calculation processes may be the physiological signals collected by the collection module 110 or physiological signals analyzed by the analysis module 120. Other physiological signals of the living organism stored in the server 170 may also be called. Other physiological signals of the living organism stored in the storage device of the vital sign obtaining system may also be called. A plurality of physiological signals may be called using the plurality of calling paths alternately. Various calculation methods or calculation processes in the calculation module 130 described above may not be essential. It will be apparent to those skilled in the art that various modifications and variations can be made in the form and details of the modules after understanding the contents and principles of the present invention without departing from the principles and the structures of the present invention, and the modifications and variations are still within the protection scope of the claims of the present invention. For example, other calculated vital sign values may be called in a process of calculating a certain vital sign, and similarly, the vital sign value may also be used as original or intermediate data in a calculation process of other vital sign values. A final calculation result of the module may be one vital sign, also may be a variety of vital signs.

The output module 140 may be configured to output the physiological signals analyzed, calculated and/or processed by the analysis module 120, and may also output the vital signs calculated by the calculation module 130. A process of outputting data by the output module 140 may be wired or wireless. The data may be outputted to a local or mobile terminal such as a desktop computer, a laptop, a mobile phone and a tablet computer, and may also be outputted to a remote server or a cloud server. The data may be outputted to other external devices connected with the vital sign obtaining system. Display forms of the outputted data may include, but are not limited to, a light emitting diode (LED), a liquid crystal display (LCD) and other electronic display screens, a resistance technology touch screen, a capacitive technology touch screen, a plasma touch screen, a vector pressure sensing technology touch screen, an infrared technology touch screen and other touch screens. Specific examples thereof may include, but are not limited to, a computer monitor, a mobile phone screen, a display screen of a tablet computer, a display screen of an electronic watch, a display screen of a blood pressure measurement instrument, a display screen of an electrocardiogram detector, a display screen of a pulse detection device, or the like. The outputted signals may be in the form of a digital form, a waveform form, an analog waveform form, a symbol form, a code form, a voice form, a video form and an image form. The types of the outputted signals may include, but are not limited to, one or more vital signs of a blood pressure, a pulse rate (PR), blood oxygen saturation, cardiac rate variability, heart murmur, bowel sounds, a pH value, a creatinine content, a transferase content, a body temperature and a carcinoembryonic antigen content. The output process may be real-time, and may also be non-real-time. The process may be implemented by the system directly, or may be implemented by an externally connected device.

The external device 150 may generally refer to various devices that are directly or indirectly connected to one or more modules of the vital sign obtaining system. The connection may be local or remote, wired or wireless. For example, the external device 150 may be a light emitting diode (LED), a liquid crystal display (LCD) and other electronic display screens, and a resistance technology touch screen, a capacitive technology touch screen, a plasma touch screen, a vector pressure sensing technology touch screen, an infrared technology touch screen and other touch screens which are used to display physiological signals. The external device may be a storage device for storing physiological signals, such as a portable hard disk, a floppy disk, a disk, a random access memory (RAM), a read-only memory (ROM) or a cloud drive, and may also be a mobile or local terminal that can implement the above-mentioned functions, such as a desktop computer, a laptop, a mobile phone or a tablet computer. The electric power 160 may generally refer to all devices that can provide power, may be wired or wireless, and may be an external AC electric source for household or industrial use, or a lithium-ion battery and other batteries. The server 170 may be configured to store all of the data related in the operational process of the vital sign obtaining system, and may provide data support for each module in the system in real time or non-real-time. The server 170 may also serve as a database of the system. The server 170 may be a local server or a cloud server, and may serve as a cloud database of the system.

The engine 100 may be provided with a corresponding storage module (not shown), or each module in the engine 100 may integrate a corresponding storage unit (not shown), so as to implement various real-time or non-real-time data generated in the operational process of the system, or to implement cache data generated in each step of the operational process of the system. The storage module or storage unit may be various storage devices such as a portable hard disk, a floppy disk, a disk, a random access memory (RAM), a read-only memory (ROM) or a cloud drive. It should be noted that the storage module or storage unit may not be essential, and the storage function may also be implemented by the external device 150 or the server 170. For example, the function may be implemented through cloud storage. The cloud storage is mainly implemented by connecting one or more remote servers through the Internet to store and process data in real time or non-real-time. The data generated during operational processes of the engine 100 or the system as well as corresponding analysis results, calculation results, processing results, calculated vital signs or the like may be stored in a personal cloud. Access to the personal cloud here requires identification. Similarly, it may also be stored in a public cloud, and access to the public cloud may require or not require identification.

The connection between the collection module 110, the analysis module 120, the calculation module 130 and the output module 140 may be wired or wireless. The modules may be connected to different electric sources separately, and every two of the modules, every three of the modules, or all of the four modules may share the same electric source. The collection module 110, the analysis module 120, the calculation module 130 and the output module 140 may be connected with different external devices separately, or may be connected with the same external device, or may be connected with the same or different external devices in any combination. The external device 150 may be connected with one or more modules, and a mode of connection may be wired or wireless. A mode of connection between the engine 100 and the server 170 may be wired or wireless. The server 170 may be local or remote. Each module and device described above may not be essential, and it will be apparent to those skilled in the art that various modifications and variations can be made in the form and details of the system after understanding the contents and principles of the present invention without departing from the principles and the structures of the present invention. Each module may be arbitrarily combined and the a few modules may be added or subtracted as needed, and these modifications and changes are still within the scope of the claims of the present invention. For example, the collection module 110 and the output module 140 may be integrated into a separate module, which has the functions of collecting signals and outputting signals. The module may be wired or wirelessly connected with the analysis module 120 and the calculation module 130. Each module may be integrated into a corresponding storage unit for temporary caching of information data generated in an execution process of the system or long-term storage of information data. The engine 100 may also be provided with a corresponding independent storage module, which is configured to store the collected and obtained, and/or analyzed and processed physiological signals, and/or the calculated vital signs. The modifications and variations are still within the protection scope of the claims of the present invention.

The connection between each module in the system for obtaining vital signs, the connection between the modules and the external devices, as well as the connection between the system and the storage device or server are not limited to the above description. The modes of connection may be used singly in the obtaining system, and also may be used in combination with various modes of connection. Each module may also be integrated together to implement the function of more than one module through the same device. The external devices may also be integrated in the implementation device of one or more modules, and single or a plurality of modules may also be integrated in single or a plurality of external devices. The connection between each module in the system, the connection between the modules and the external devices, as well as the connection between the system and the storage device or server may be either wired or wireless. The wired connection may include, but is not limited to, a wired connection such as a wire and an optical fiber, and the wireless connection may include, but is not limited to, a wireless connection including various radio communications such as Bluetooth and infrared.

The engine 100 may include one or more processors. Each module or unit of the engine 100 may be implemented on one or more processors. For example, the collection module 110, the analysis module 120, the calculation module 130 and the output module 140 may be implemented on one or more processors. One or more processors may communicate with the storage device (not shown), the external device 150, or the server 170. The processor may read signal or compute program instructions from the storage device (not shown), the external device 150 or the server 170 and perform analysis, calculation or processing on the read signals as described elsewhere in the text to obtain one or a set of vital signs, or other information than can be obtained through the system. The processor may be wired or wirelessly connected to other devices that may be directly or indirectly related to the system, such as a smartphone APP, a care facility of a medical treatment institution, a local or remote computer client, or the like, and information sharing with the devices may be implemented.

Figure 2:
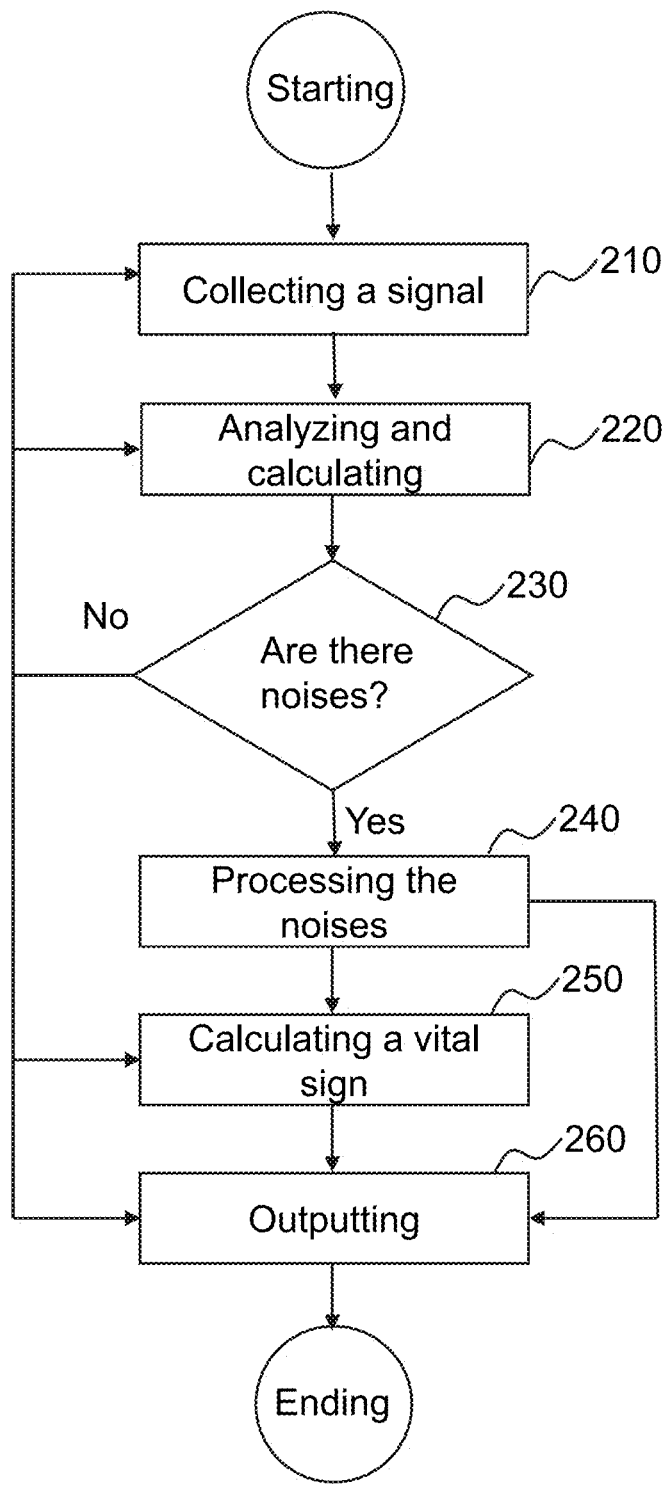
FIG. 2 is a schematic diagram of a method.

FIG. 2 is a schematic diagram showing a method for obtaining vital sign by the system. The method may include the following operation: physiological signals or non-physiological signals of a living organism may be collected at step 210. The types of the physiological signals may include, but are not limited to, pulse waves, electrocardiogram, a cardiac rate, a blood pressure, blood oxygen, respiration, a height, a weight, a body temperature, a musculoskeletal state, brain waves, a fat content, a blood sugar concentration, a blood concentration and blood flow. The non-physiological signals may include, but are not limited to, a moving/vibrating signal of the living organism. The collection of the physiological signals or non-physiological signals may be implemented by the collection module 110. The system may analyze and calculate the signals (step 220). Feature analysis of the collected signals may be implemented at step 220. The feature results may include, but are not limited to, a waveform, a wave crest, a wave trough, peak amplitude, peak point spacing, a phase, a frequency, a period, or the like, or any combination thereof. The analysis and calculation may be implemented by the analysis module 120. The analysis and calculation processes may be in real-time or non-real-time. After various feature analysis of the received signal is completed at step 220, whether there is a noise in the received physiological signals is judged at step 230. If it is judged that there is no noise in the physiological signal, step 260 is performed directly, and the physiological signals are outputted. The physiological signals may be outputted by the output module 140. In this case, the process may return to step 210 and continue to collect a new signal, for example, start a new process. In this case, the process may return to step 220 so as to analyze the collected next signal or next group of signals. In this case, the process may return to step 220 so as to analyze the collected next signal or next group of signals. The vital signs may be calculated by the calculation module 130. If it is judged that there is a noise in the physiological signal at step 230, step 240 is performed, and the collected physiological signals are subjected to noise process. The noise process may be implemented the analysis module 120. The noise processed physiological signal may be transmitted to a storing step (not shown) and stored in a corresponding storage device. The storage device may be the external device 150 mentioned above, a storage unit (not shown) integrated in the collection module 110, a separate storage module (not shown) of the engine 100, the server 170, or a storage unit (not shown) integrated by each module of the engine 100. The physiological signal after the noise process performed at step 240 may be outputted at step 260. The noise processed physiological signal may also be transmitted to step 250, and vital signs may be obtained by calculation using the noise processed physiological signal. The calculated vital signs may be outputted at step 260. The methods and steps described herein may be implemented in any suitable order, or simultaneously, where appropriate. In addition, the individual steps may be eliminated from either method without departing from the spirit and scope of the subject matter described herein. Aspects of any example described above may be combined with aspects of any of the other described examples to constitute further examples without losing the desired effect. For example, a preprocessing step may be added between step 210 and step 220, and the preprocessing step may be used to perform a preliminary coarse smoothing or remove significant interference process on two or more collected signals. The processing method may include, but is not limited to, low-pass filtering, bandpass filtering, wavelet transform filtering, a median filtering method, morphological filtering and a curve fitting method. In addition, other selecting or processing steps may be added between step 210 of collecting a signal and step 220 of analyzing and calculating. For example, the two or more collected signals may be stored and backed up. Similarly, the storing and backing up step may be added between any two steps in the flowchart. In addition, step 230 may not be essential, and the noise judgment step may be skipped so as to perform the next step of noise process. Step 240 of noise process may call one or more processing methods, the methods may be independent of each other or may be related to each other, and data generated in the process may be supported as data of other processing methods. Similarly, data generated in other processing methods may also be called.

Figure 3:
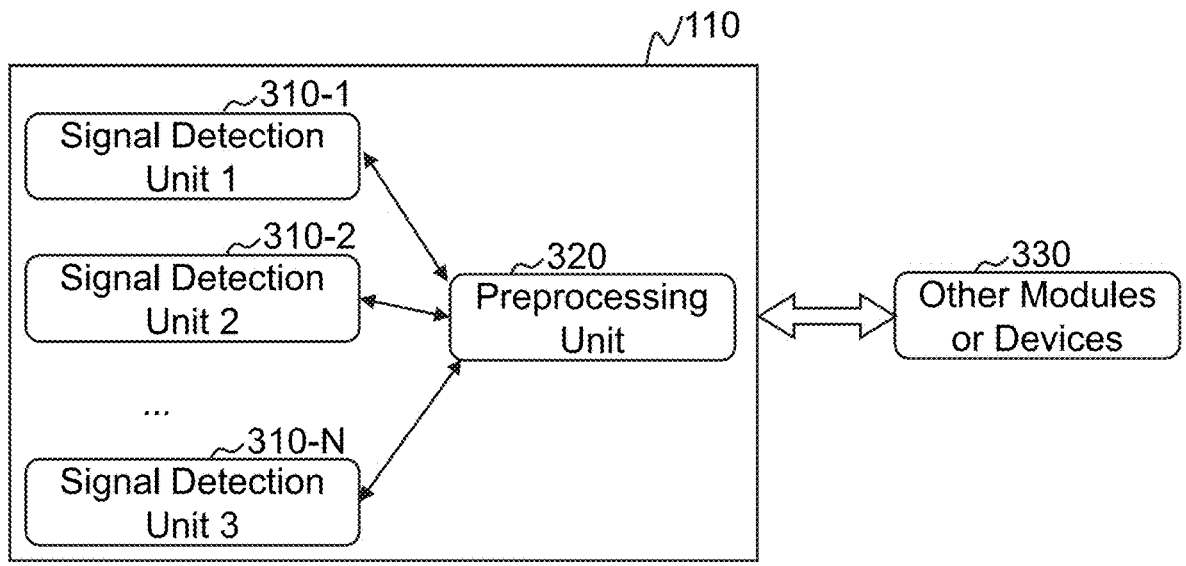
FIG. 3 is a schematic diagram of a collection module.

FIG. 3 is a schematic diagram of a collection module. The collection module 110 may include one or more signal detection units as indicated by 310-1, 310-2, . . . 310-N in the figure. The one or more signal detection units may be configured to detect physiological signals of a living organism, such as a PPG signal of the living organism. The detectable physiological signals of the living organism here may be detected from the same location of the living organism, and may also be detected from different locations of the living organism. The one or more signal detection units may be configured to detect other non-physiological signals of the living organism, such as a moving/vibrating signal. The one or more signal detection units may be configured to detect or store a reference signal, such as a signal received directly by a receiver after being transmitted by a transmitter. The signal detection units may be independent of each other, or related to each other, and may also be integrated in the same signal detection unit. One signal detection unit may adopt one or more signal detection methods. Similarly, each signal detection unit may adopt the same signal detection method or different signal detection methods. Each signal detection unit may include an individual Analog/Digital sampling unit (an A/D sampling unit) (not shown), and every two of the signal detection units, every three of the signal detection units, or all of the signal detection units may share the same Analog/Digital sampling unit (not shown). The signal detection units may share the same light source transmitter (not shown), or may use different light source transmitters (not shown) separately. The signal detection units may share the same sensor receiver (not shown), or may use different sensor receivers (not shown) separately. Similarly, the light source transmitters (not shown) and sensor receivers (not shown) may be arranged and combined in any form so as to achieve a better signal detection effect. The preprocessing unit 320 may be configured to preliminarily preprocess the collected signal. The preprocessing may achieve an effect of smoothing the signal or removing significant interference. The preprocessing method may include, but is not limited to, low-pass filtering, bandpass filtering, wavelet transform filtering, a median filtering method, morphological filtering, a curve fitting method, or any combination thereof. The collection module 110 may be wired or wirelessly connected with other modules or devices 330 so as to implement data transmission in real-time or non-real-time. The description of the collection module 110 may only be a specific example, and should not be taken as the only possible implementation. Every module or unit mentioned above may be implemented through one or more components, and functions of each module or unit may not be limited thereto. Obviously, to those skilled in the art, after understanding the basic principle of signal collection, various modifications and variations can be made in the forms and details of specific implementation manners and steps of the collection module without departing from the principle. It is also possible to make some simple deductions or replacements that make certain adjustments or combinations of an order of the modules or units without any creative work, but these modifications and variations are still within the scope of the above description. For example, each signal detection unit may be provided with a corresponding smoothing unit or a preprocessing unit (not shown) to perform simple smoothing or coarse filtering process on the collected signal, so as to achieve an effect of smoothing the signal or removing significant interference. Similarly, the preprocessing unit 320 may also be integrated in one or more signal detection units. Similarly, the preprocessing unit 320 may not be essential, and may be implemented by an external device connected with the collection module 110. In addition, Analog/Digital sampling units included or used in each signal detection unit may not be essential. The collection module 110 may not only implement the collection of digital signals, but also implement the collection of analog signals. The type of the collected signal may not affect a step after the signal is collected or the implementation of functions of modules or devices other than the collection module. The collection module 110 may use the collected physiological signals or non-physiological signals and the reference signal to calculate signals that are absorbed or depleted by the living organism in different processes.

Figure 4:
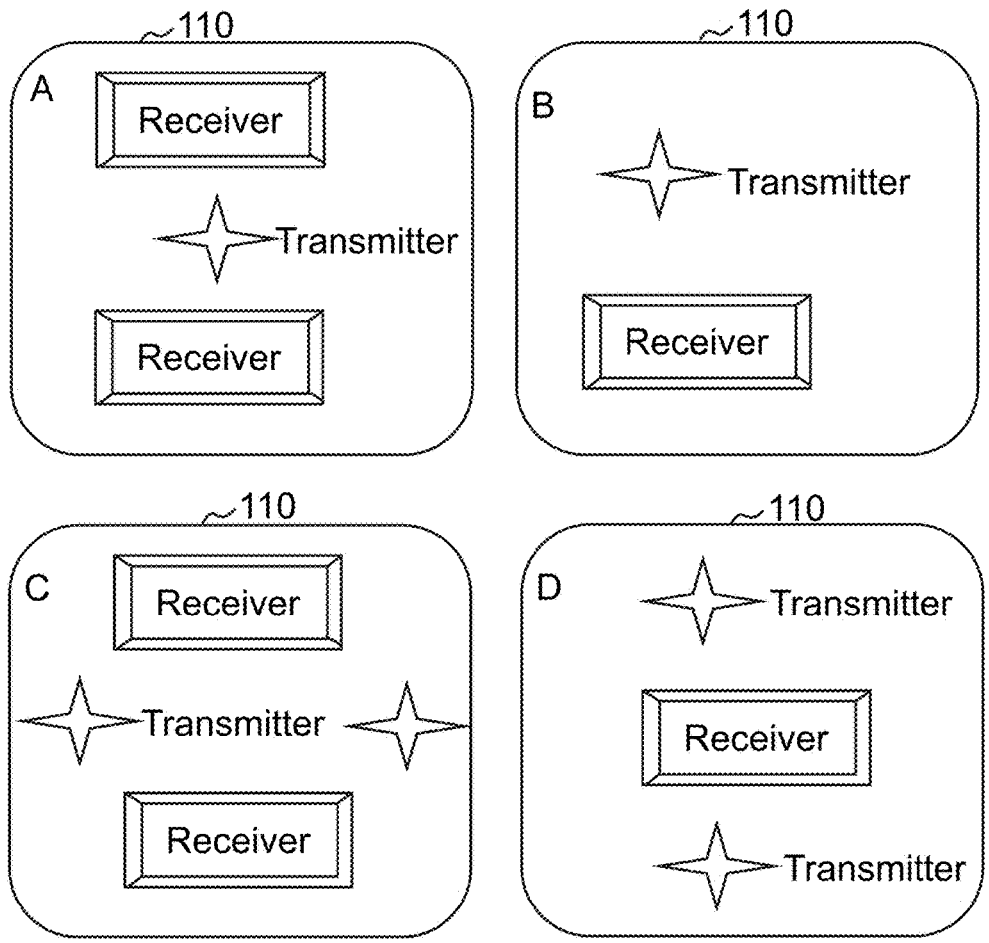
FIG. 4 is a schematic diagram of an application embodiment of the collection module.

FIG. 4 shows a schematic diagram of four specific embodiments of the collection module 110. Plan A may include one transmitter and two receivers. Plan B may include one transmitter and one receiver. Plan C may include two transmitters and two receivers. Plan D may include two transmitters and one receiver. The four cases listed in the figure may only represent a few possible implementation schemes of the collection module 110 and do not imply that the specific embodiment of the collection module 110 is limited to the above cases. Plan A may be taken as an example, in which one transmitter and two receivers are included. The transmitters may be different types of light sources with different wavelengths in different frequency bands, and the light sources belong to spectrums of different frequency bands, including but not limited to a visible spectrum, an infrared spectrum, a far-infrared spectrum or the like. The types of beams of light are specifically, but not limited to, red light, green light, infrared light, blue light, violet light, yellow light, orange light, and cyan light. The receiver may be different types of sensor, and may include but is not limited to a photoelectric sensor, a displacement sensor, an acceleration sensor, a vibration sensor, a mechanical sensor, a temperature sensor and a gas sensor. Types of the photoelectric sensor may include, but is not limited to, a diffuse reflectance photoelectric sensor, a Thru-beam photoelectric sensor, a distance photoelectric sensor, a trough photoelectric sensor and an optical fiber photoelectric sensor. In the process of collecting a signal, the transmitter is placed near the skin of a living organism to be detected, and the transmitter may transmit two beams of light of the same type simultaneously or two beams of light of the same type time sharing. The two beams of light may reach the skin of the living organism simultaneously or in time-sharing, and penetrate the skin to reach blood vessels under the skin of the living organism. The two beams of light may be received by the two receivers separately after being reflected by the living organism. Parameter states of the two receivers may be different. The two receivers may be adjusted to different parameter states by adjusting parameters such as, but not limited to, resistivity, current, voltage and sensitivity of light intensity. Since the parameter states of the two receivers are different, the sensitivities of signal intensity thereof are different. A PPG signal of the living organism belongs to a low-frequency physiological signal and signal intensity thereof is relatively weak, and therefore the PPG signal of the living organism may not be received or detected when the sensitivity of the receiver is relatively low. Therefore, in the present embodiment, a signal received by a first receiver is a physiological signal of the living organism, including a PPG signal of the living organism and a moving/vibrating signal of the living organism, and a signal received by a second receiver may include a moving/vibrating signal of the living organism.

Similarly, plan B may include one transmitter and one receiver. The transmitter may transmit two beams of light of the same type time sharing. A first beam of light may reach the skin of the living organism, penetrate the skin to reach blood vessels under the skin, and being received by the receiver after being reflected by the living organism. At this moment, the receiver is in a first parameter state, and the first signal received is a physiological signal of the living organism, including a PPG signal of the living organism and a moving/vibrating signal of the living organism. The transmitter may transmit a second beam of light, and the second beam of light may reach the skin of the living organism and being received by the receiver after being reflected by the living organism likewise. At this moment, the receiver is adjusted to a second parameter state, and similar to the plan A described above, sensitivity of the receiver is reduced after the parameter state of the receiver is changed and the PPG signal of the living organism may not be received or detected. Therefore, in the present embodiment, the received second signal may include a moving/vibrating signal of the living organism, and differences of the second parameter state and the first parameter state may include, but are not limited to, resistivity, current, voltage, sensitivity of light intensity, or any combination thereof.

Plan C of the collection module 110 may include two transmitters and two receivers. The two transmitters may transmit two beams of light with different features such as, but not limited to, infrared light and green light, red light and green light, infrared light and red light. The two beams of light may be in the same phase or in different phases; may have different wavelengths or the same wavelength; may be in different frequency bands or the same frequency band; and may have the same intensity or different intensities. In particular, the two beams of light may also be obtained by adding the same or different carrier signals to one or more original beams of light/signals and performing modulation. For example, spectrums of the original beams of light/signals may be moved to any spectral range through frequency modulation, phase modulation, amplitude modulation, etc., which facilitates the beam of light/signal transmission. The two different beams of light may be transmitted to the skin of the living organism, and since penetrating capacities of the two beams of light are different, a first beam of light may penetrate a skin surface layer and reach blood vessels under the skin, while a second beam of light may be reflected directly on the skin surface, or the surface of skin. At this moment, parameter states, resistivity, current, voltage and sensitivity of light intensity of the two receivers are all the same, but the two receivers may receive two different signals. The beam of light that penetrates the skin surface layer and reaches depth of the skin is received by the first receiver after reflected by the living organism, and the first signal received by the first receiver is a physiological signal of the living organism, including a PPG signal of the living organism and a moving/vibrating signal of the living organism. The beam of light directly reflected on the skin surface by the living organism is received by the second receiver, and the second signal received by the second receiver may include a moving/vibrating signal of the living organism.

Similarly, plan D may include two transmitters and one receiver. The two transmitters may transmit two beams of light with different features such as, but not limited to, infrared light and green light, red light and green light, infrared light and red light. The two beams of light may be in the same phase or in different phases; may have different wavelengths or the same wavelength; may be in different frequency bands or the same frequency band; and may have the same intensity or different intensities. In particular, the two beams of light may also be obtained by adding the same or different carrier signals to one or more original beams of light/signals and performing modulation. For example, spectrums of the original beams of light/signals may be moved to any spectral range through frequency modulation, phase modulation, amplitude modulation, etc., which facilitates the beam of light/signal transmission. The two different beams of light may be transmitted to the skin of the living organism, and since penetrating capacities of the two beams of light are different, a first beam of light may penetrate a skin surface layer and reach blood vessels under the skin, while a second beam of light may be reflected directly on the skin surface. Subsequently, the two beams of light are received by the receiver time sharing after being reflected by the living organism. A first beam of light may penetrate the skin surface layer and reach blood vessels under the skin, and a reflection signal reflected by the living organism is a physiological signal of the living organism, including a PPG signal of the living organism and a moving/vibrating signal. A second beam of light is directly reflected on the skin surface by the living organism, and a reflection signal received by the receiver may include a moving/vibrating signal of the living organism.

The above description of specific embodiments of the collection module 110 is merely exemplary, and it should be understood that feasible implement schemes are not limited thereto. Every module or unit mentioned above may be implemented through one or more components, and functions of each module or unit may not be limited thereto. Obviously, to those skilled in the art, after understanding the basic principle for collecting signals of the living organism, various modifications and variations can be made in the forms and details of specific implementation manners and steps of the collection module without departing from the principle. It is also possible to make some simple deductions or replacements that make certain adjustments or combinations of an order of the modules or units without any creative work, but these modifications and variations are still within the scope of the above description. For example, the various schemes are based on an example in which two signals are collected, but it does not mean that the number and types of signals collected by the collection module 110 are limited thereto. All of the schemes are applicable to cases in which two or more signals are collected. The collection module 110 may include one or more transmitters and one or more receivers, and the transmitters and receivers may be arranged and combined in any form so as to achieve a better effect of signal collection. The transmitter and receiver may be integrated in the same photoelectric sensor, or may be provided to different photoelectric sensors or other devices separately. The function of collecting two signals described above may also be implemented by using one transmitter and one receiver, and the transmitter may transmit two beams of light of different intensities by adjusting the intensity of excitation current at the transmitter. The two beams of light of different intensities may have different penetrating capacities, and therefore the same effect as described above may be achieved after the beams of light are reflected by the living organism. The modifications and variations are still within the protection scope of the present invention.

Figure 5:
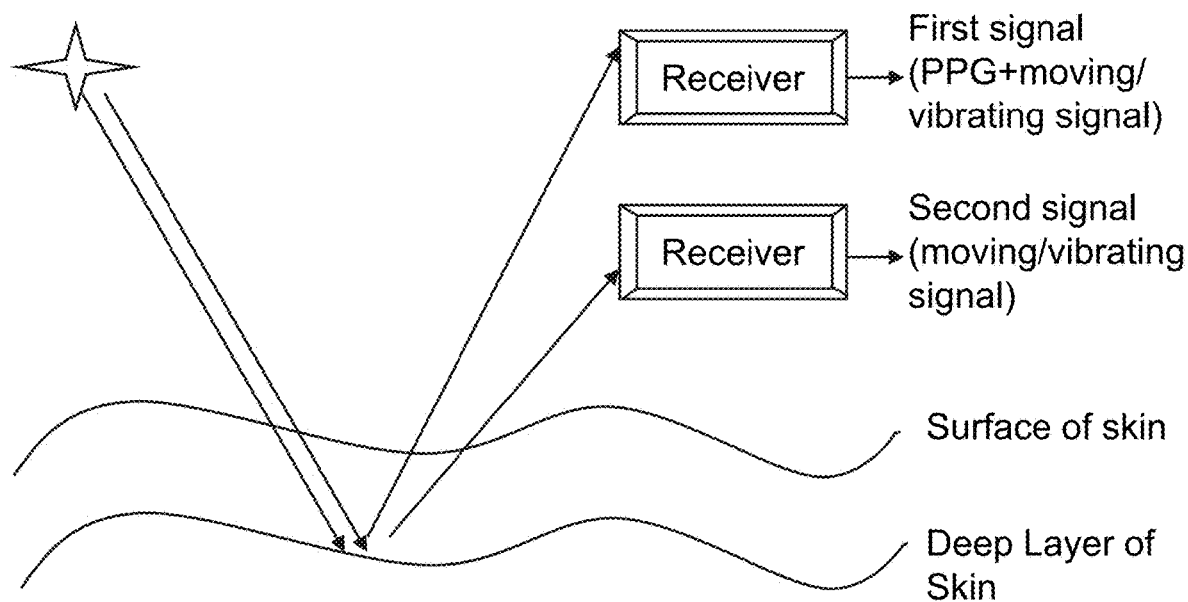
FIG. 5 is a schematic diagram of a process of using a light source to collect two signals.

FIG. 5 is a schematic diagram of collecting two signals by the collection module. Plan A in FIG. 4 is taken as an example in the figure, and an example of collecting two signals is given, which does not mean that the manner and form of collecting two signals are limited to those shown in the figure. As shown in FIG. 5, the transmitter may transmit two beams of light of the same type simultaneously or two beams of light of the same type time sharing. The transmission routes of the two beams of light are the same, and the two beams of light may penetrate the skin surface of the living organism, reach the blood vessels under the skin, and being received by the receiver after reflected by the living organism. Here, at least one of the parameters of the two receivers including resistivity, current, voltage and sensitivity of light intensity is different. Since a PPG signal of the living organism belongs to a low-frequency physiological signal and signal intensity thereof is relatively weak, the PPG signal of the living organism may not be received or detected when the sensitivity of the receiver is relatively low. Two receivers with different parameter states (for example, different sensitivities) may receive two different signals. A first signal received by a first receiver is a physiological signal of the living organism, including a PPG signal of the living organism and a moving/vibrating signal of the living organism, and a second signal received by a second receiver may include a moving/vibrating signal of the living organism.

Figure 6:
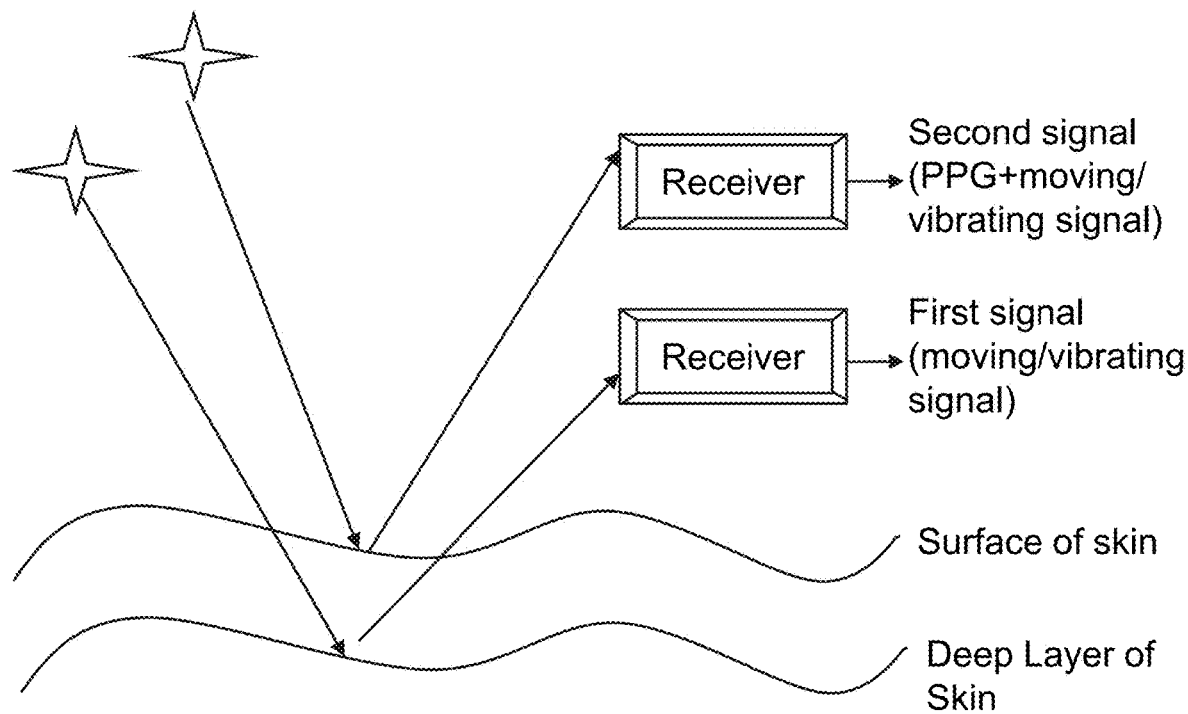
FIG. 6 is a schematic diagram of a process of using two light sources to collect two signals.

FIG. 6 is another schematic diagram of collecting two signals by the collection module. Plan C in FIG. 4 is taken as an example in the figure, and a process of collecting signals in which two transmitters and two receivers are used is given. As shown in FIG. 6, the two transmitters may transmit two different types of beams of light with different wavelengths in different frequency bands such as, but not limited to, red light and infrared light, red light and green light, green light and infrared light. A first beam of light may penetrate the skin surface layer of the living organism, reach blood vessels under the skin, and being received by a first receiver after reflected by the living organism. The received signal is a first signal, for example, a physiological signal of the living organism including a PPG signal of the living organism and a moving/vibrating signal of the living organism. A second beam of light is directly reflected on the skin surface by the living organism without penetrating to the blood vessels, and a second signal received by the second receiver may include a moving/vibrating signal of the living organism.

Only two specific examples are given in FIGS. 5 and 6, and it does not mean that the transmission between the beam of light and the living organism is limited thereto. The cases listed above should not be considered as the only feasible implement scheme. It would be apparent to those skilled in the art that after knowing the basic principle of photoelectric sensing, various modifications and variations in the form and details of the implement manners and steps of collecting a signal may be made, and simple deductions or replacements may be made without departing from the basic principle, and the type or location of the transmitter or receiver may be adjusted or combined without creative efforts, but the modifications and variations are still within the scope of the above description. For example, the case shown in FIG. 5 may also use one receiver only, for example, as indicated by plan B in FIG. 4, two beams of light of the same type with the wavelength in the same frequency band may be transmitted by the light source transmitter time sharing, and after being reflected by the living organism, the two signals are received, in time sharing, by one receiver in which at least one of the parameters including resistivity, current, voltage and sensitivity of light intensity is adjusted. Similarly, the case shown in FIG. 6 may also use the same receiver whose parameter states such as resistivity, current, voltage and sensitivity of light intensity are not changed, for example, as indicated by plan D in FIG. 4, one receiver may receive two signals reflected by the living organism in time sharing.

Figure 7:
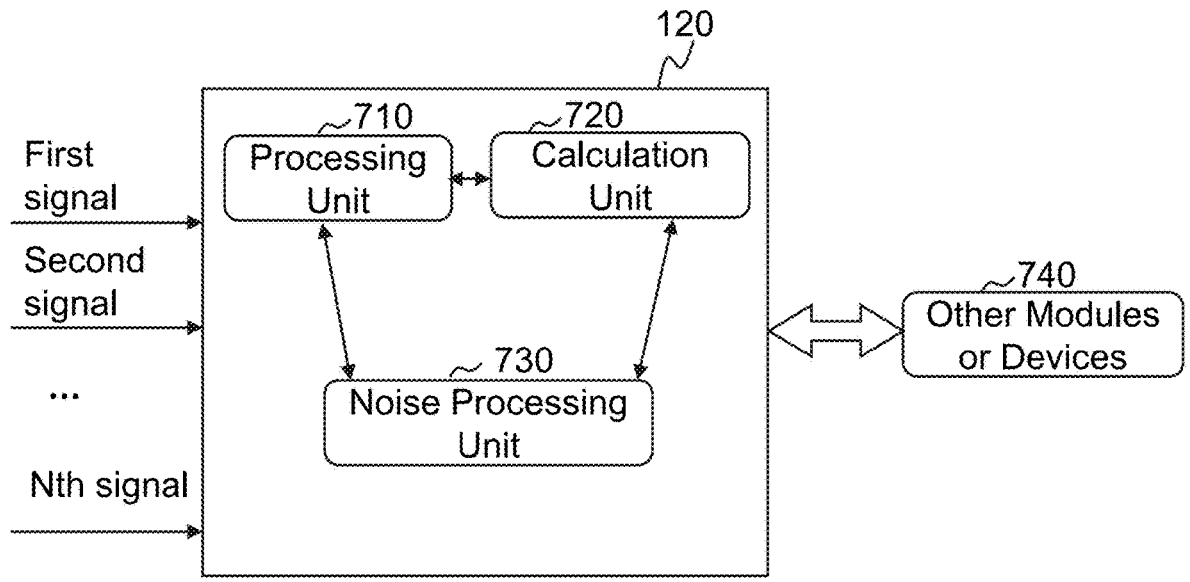
FIG. 7 is a schematic diagram of an analysis module.

FIG. 7 is a schematic diagram of the analysis module 120. The analysis module 120 may include a processing unit 710, a calculation unit 720 and a noise processing unit 730. The processing unit 710 may be configured to perform feature analysis on received first signal to Nth signal. The used analysis method may include, but is not limited to, sample analysis, grid analysis, feature point extraction, regression analysis, Gaussian process regression analysis, variance analysis, mean analysis, cluster analysis, a linear discriminant algorithm, multiple linear principal component analysis, factor analysis, discriminant analysis, comparative analysis, analog analysis, simulation analysis, threshold method, Gaussian function decomposition, Wavelet transform, Fourier transform, Chebyshev polynomial fitting, a QRS wave detection algorithm, a peak detection algorithm, an HTT method, second discriminant analysis, a maximum entropy classifier, a decision tree, a decision table, kernel estimation, a nearest neighbor method, a naive Bayesian classifier, a neural network, a vision sensor, a gene expression programming, a Markov random field, a Kalman Filter, a particle filter, independent component analysis, principal component analysis, a condition random domain, a Hidden Markov model, a maximum entropy Markov model, a recurrent neural network, a relational rule, inductive logic programming, similarity measure learning, a deep neural network, a deep belief network, a convolutional neural network, a convolution depth belief network, or the like, or any combination thereof. The calculation unit 720 may calculate the received first signal to Nth signal directly, or may also calculate signals subjected to the feature analysis. The calculation method may include, but is not limited to, min-max normalization, Z-score normalization, normalization by fractional scaling, a linear function method, a logarithmic function method, an anti-cotangent function method, a norm method, historical threshold iteration, a modeling method, a least square method, an elimination method, a reduction method, a substitution method, an image method, a comparative method, a scaling method, a vector method, an inductive method, reduction to absurdity, an exhaustion method, a matching method, a method of undetermined coefficients, a method of element changing, a term split method, a term filling method, a factorization method, a parallel translation method, a function approximation method, an interpolation method, a curve fitting method, an integral method, a differentiation method, a perturbation method, or the like, or any combination thereof. The calculation unit 710 may also be configured to perform adjustment process on the received first signal to Nth signal, and the content of the adjustment process may include, but is not limited to, amplitude, a phase, a frequency, intensity, or any combination thereof. The manner of the adjustment process may include, but is not limited to, angle modulation, phase modulation, frequency modulation, amplitude modulation, double-sideband modulation, single-sideband modulation, vestigial sideband modulation, amplitude offset modulation, phase offset modulation, quadrature amplitude modulation, frequency offset modulation, continuous phase modulation, orthogonal frequency division multiplexing, pulse code modulation, pulse width modulation, pulse amplitude modulation, pulse position modulation, pulse number modulation, trigonometric integral modulation, or any combination thereof. Accordingly, the calculation unit 710 may also perform demodulation process on the received first signal to Nth signal to decompose a modulated original signal. The noise processing unit 730 may be configured to perform noise process on the signal. The method of noise process may include, but is not limited to, a reference signal removing method, a method of compensation, a high-pass filtering method, an FIR filtering method, a curve fitting method, a wavelet filtering method, an adaptive filtering method, a median filtering method, a morphological filtering method, and in particular, a method of performing subtraction or addition on two or more signals, or combination thereof. The processing unit 710, the calculation unit 720 and the noise processing unit 730 may transmit data in real time or non-real-time among two or three of the units. The analysis module 120 may be wired or wirelessly connected with other modules or devices 740. For example, the analysis module 120 may be wired or wirelessly connected with one or more modules in the calculation module 130, the output module 140 and the external device 150 so as to implement data transmission in real-time or non-real-time. The description of the analysis module 120 may only be a specific example, and should not be taken as the only possible implementation. Every module or unit mentioned above may be implemented through one or more components, and functions of each module or unit may not be limited thereto. It would be apparent to those skilled in the art that after knowing the basic principle of analyzing a signal, various modifications and variations in the form and details of the implement manners and steps of the analysis module 120 may be made, and simple deductions or replacements may be made without departing from the basic principle, and an order of each module or unit may be adjusted or combined without creative efforts, but the modifications and variations are still within the scope of the above description. For example, the processing unit 710 and the calculation unit 720 may be integrated in the same unit which has the functions of signal analysis and calculation. Similarly, two or three of the processing unit 710, the calculation unit 720 and the noise processing unit 730 may be integrated in the same unit which has the function of each unit. The analysis module 120 may be provided with a corresponding storage unit (not shown) to implement data generated or related in the operational process of the module or each unit in real-time or non-real-time.

Figure 8:
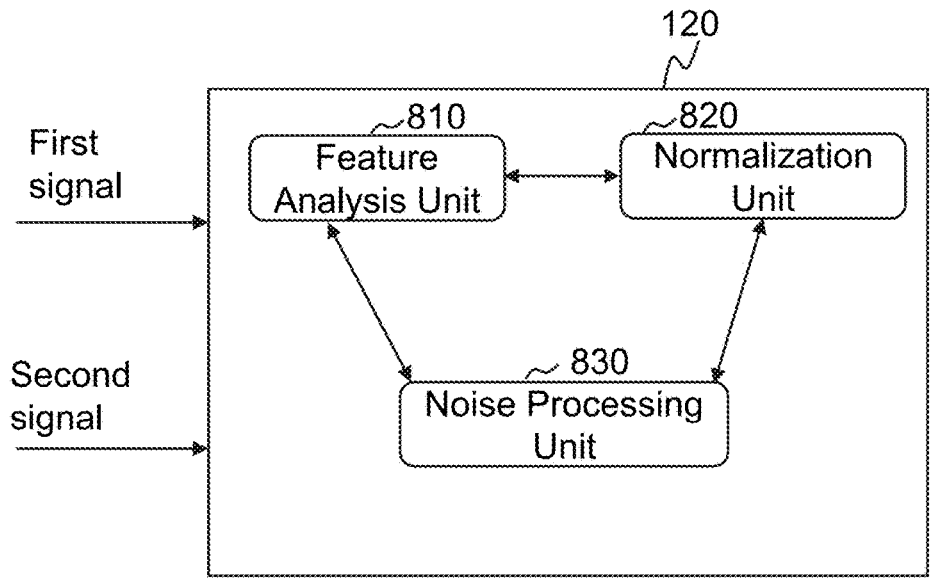
FIG. 8 is a schematic diagram of an application embodiment of the analysis module.

FIG. 8 is a schematic diagram of a specific embodiment of the analysis module 120. The analysis module 120 may include a feature analysis unit 810, a normalization unit 820 and a noise processing unit 830. The feature analysis unit 810 may be configured to perform feature analysis on the received signal. The feature analysis may include, but is not limited to, a waveform, a wave crest, a wave trough, peak amplitude, peak point spacing, a phase, a frequency, a period, or the like, or any combination thereof. The analyzed feature results may be displayed in a waveform graphic form or in a digital form, but the display may not be essential. The normalization unit 820 may be configured to perform normalization process on the analyzed feature results. The normalization method may include, but is not limited to, min-max normalization, Z-score normalization, normalization by fractional scaling, a linear function method, a logarithmic function method, an anti-cotangent function method, a norm method, or the like, or any combination thereof. The noise processing unit 830 may be configured to perform noise process on physiological signals. For example, in two signals collected by the collection module 110, a first signal is a physiological signal of the living organism, and a second signal is a non-physiological signal such as a moving/vibrating signal of the living organism. During the noise process, the second signal is taken as a reference signal, and a noise in the first signal, for example, a physiological signal of the living organism is removed. Further, a corresponding relation coefficient unit (not shown) may be used during the noise process. Different relation coefficients may be selected to perform the noise process based on a type of the light source transmitter as well as parameters such as resistivity, current, voltage and sensitivity of light intensity of the sensor receiver used during the process of collecting a signal. The relation coefficient unit (not shown) may be integrated in the noise processing unit 830, may be an individual unit in the analysis module 120, may be integrated in other units, and may also be implemented by the external device 150. The analysis module 120 may be wired or wirelessly connected with other modules or devices (not shown) so as to implement data transmission in real-time or non-real-time. The description of the analysis module 120 may only be a specific example, and should not be taken as the only possible implementation. Every module or unit mentioned above may be implemented through one or more components, and functions of each module or unit may not be limited thereto. Obviously, to those skilled in the art, after understanding the basic principle of analyzing and processing a physiological signal, various modifications and variations can be made in the forms and details of specific implementation manners and steps of the analysis module 120 without departing from the principle. It is also possible to make some simple deductions or replacements that make certain adjustments or combinations of an order of the modules or units without any creative work, but these modifications and variations are still within the scope of the above description. For example, the normalization unit 820 in the analysis module 120 may not be essential and the normalization process may be implemented by the external device 150. Similarly, any one unit may be integrated in other units, and may not be necessarily individual. In addition, the analysis module 120 may be integrated with a corresponding storage unit (not shown) to store data generated in the analysis process in real-time or non-real-time. In addition, a phase adjustment unit (not shown) may be provided in the analysis module 120, or the phase adjustment unit (not shown) may be integrated in the normalization unit 820, noise processing unit 830, other modules or the external device 150. The phase adjustment unit (not shown) may implement phase adjustment on the two signals, and the adjustment method may include, but is not limited to, left-right translation of the two signal waveforms and the correspondence of feature points of the wave crest and wave trough, by which two signals are adjusted to be basically the same in phase, and any subsequent calculation, analysis or processing may be performed directly.

Figure 9:
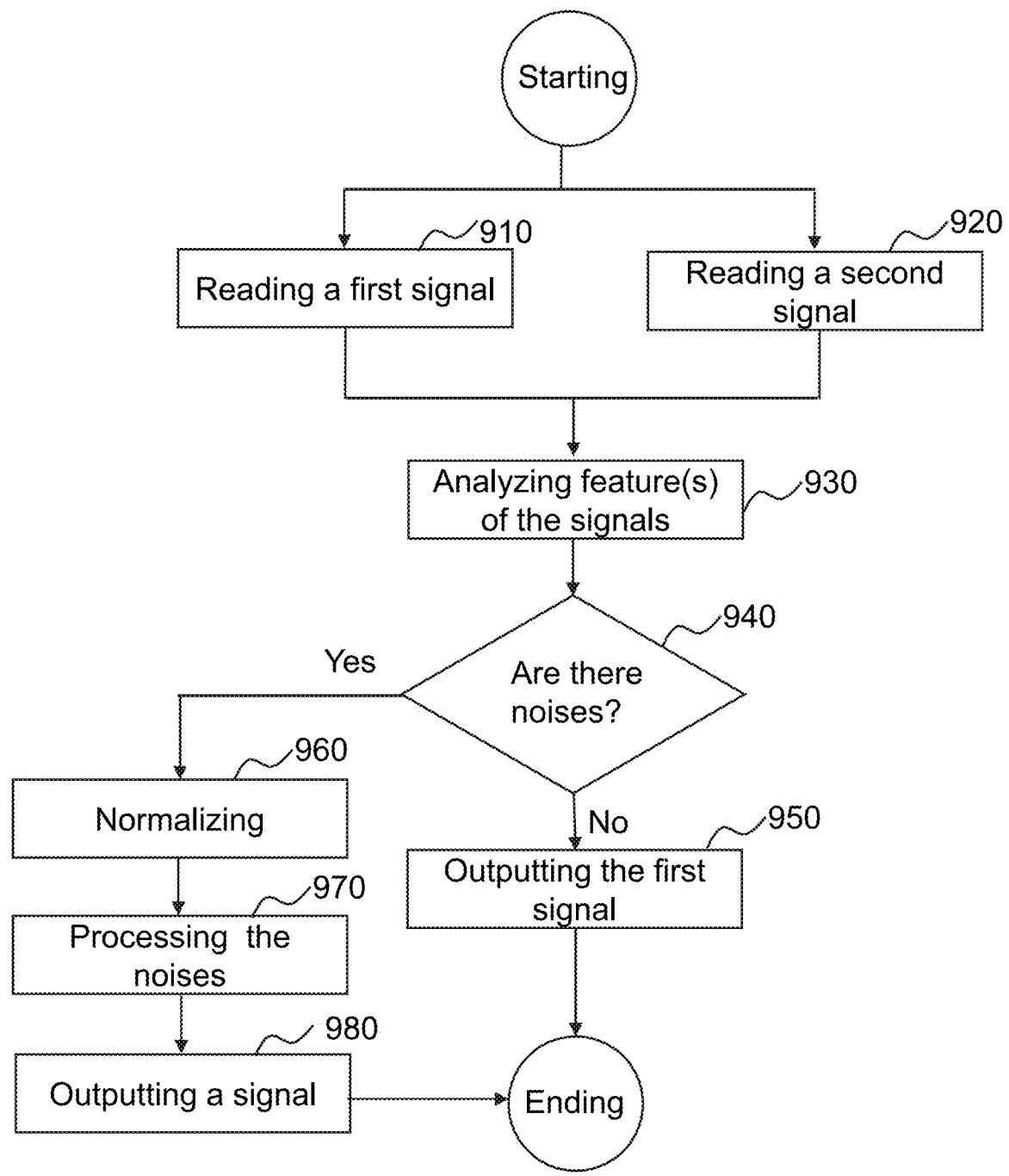
FIG. 9 is a flow chart of an application embodiment of the analysis module.

FIG. 9 is a flow chart of a specific embodiment of the analysis module 120. Firstly, step 910 and step 920 are implemented, in which a first signal and a second signal are read, the first signal being a physiological signal of the living organism. Step 910 and step 920 may be performed simultaneously or may be performed time sharing. After the two signals are read, step 930 may be implemented, and feature analysis may be performed on the two signals at step 930, the features including but not limited to a waveform, a wave crest, a wave trough, peak amplitude, peak point spacing, a phase, a frequency, a period or any combination thereof. After the feature analysis, judgment is implemented at step 940. It is judged whether there is a noise in the first signal based on the features of the two signals analyzed at step 930, and if it is judged that there is no noise, step 950 is performed directly and the first signal is outputted. If it is judged that there is a noise, step 960 is performed and the normalization process is performed on the first signal or second signal, the normalization method including but not limited to min-max normalization, Z-score normalization, normalization by fractional scaling, a linear function method, a logarithmic function method, an anti-cotangent function method, a norm method, or any combination thereof. Step 960 of normalizing may be implemented by the normalization unit 820. After the normalization process, an amplification factor of the two signal waveforms are adjusted to be consistent, for example, the original signals are standardized to be in the same order of magnitude and can be compared with each other, and further calculation may be performed. After the normalization process, step 970 of noise process is performed. At this moment, the second signal may be taken as a noise reference, and the noise in the first signal is removed. At this moment, the first signal is a physiological signal of the living organism including a noise signal, and the second signal may mainly include a noise signal. Therefore, the second signal may be taken as a reference of the noise signal, and modifications, correction and calculation may be performed on the first signal by using the reference signal, so as to achieve a purpose of removing the noise signal of the first signal. The noise processing method used in step 970 of noise process may include, but is not limited to, simple filtering, algorithm filtering, or the like. Specific algorithms may include, but are not limited to, simple mathematical operations such as various common addition, subtraction, multiplication, division, involution and radication; various operations of functions such as a linear function, a quadratic function, a cubic function, a quartic function, a quintic function, a power function, a compound function, a program function, a transcendental function and a complex function; various simulation calculation such as physical simulation, mathematical simulation, semi-physical simulation, continuous simulation, discrete simulation, analogue simulation, digital simulation, hybrid simulation, real-time simulation, ultra-real-time simulation and sub-real-time simulation or combination thereof. During the operation of various algorithms of noise process, corresponding relation coefficients may be selected and read from the relation coefficient unit (not shown) for applying according to the type of the light source, and parameters such as resistance, current, voltage and sensitivity of light intensity of the receiver. The relation coefficients may be applied to any one or more algorithm steps, may be used as initial data, and may also be configured to correct and optimize terminal data. After the noise process, step 980 is performed by the output module 140 so as to output the noise processed signal. Further, during any process of the signal analysis or processing, the first signal and the second signal may be adjusted, for example, but not limited to, adjusting amplitude, a phase, a frequency, intensity, or any combination thereof. The method of the adjustment process may include, but is not limited to, angle modulation, phase modulation, frequency modulation, amplitude modulation, double-sideband modulation, single-sideband modulation, vestigial sideband modulation, amplitude offset modulation, phase offset modulation, quadrature amplitude modulation, frequency offset modulation, continuous phase modulation, orthogonal frequency division multiplexing, pulse code modulation, pulse width modulation, pulse amplitude modulation, pulse position modulation, pulse number modulation, trigonometric integral modulation, or any combination thereof. Accordingly, during any process of the signal analysis or processing, the first signal and the second signal may be demodulated to decompose the modulated original signal. The methods and steps described herein may be implemented in any suitable order, or simultaneously, where appropriate. In addition, the individual steps may be eliminated from either method without departing from the spirit and scope of the subject matter described herein. Aspects of any example described above may be combined with aspects of any of the other described examples to constitute further examples without losing the desired effect. For example, a corresponding caching or storing step may be added between step 930 and step 940. The feature of a signal obtained by analysis at step 930 is stored, and the cached or stored data may be read at a subsequent judgment step. Similarly, a similar caching or storing step may be added between any two steps. A phase adjustment step may be added between step 960 of normalization and step 970 of noise process. By left-right translation of two signal waveforms and the correspondence of feature points of the wave crest and wave trough, the two signals are adjusted to be basically the same in phase, and subsequent steps of calculation and noise process may be performed more accurately. In addition, the judgment step 940 may not be essential, and the subsequent analysis process may be performed directly after the feature analysis.

Figure 10:
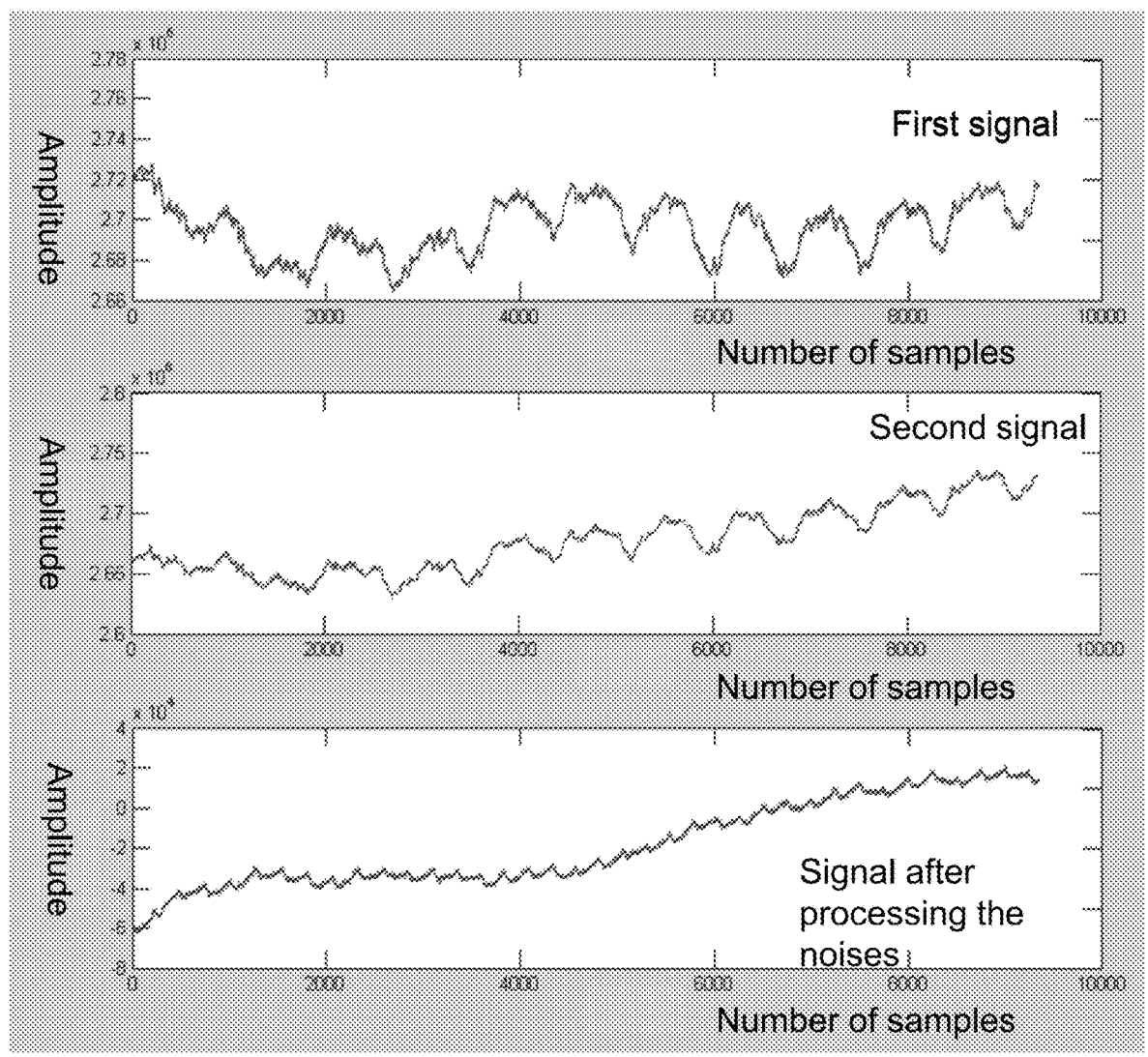
FIG. 10 is a figure showing experimental results of two collected signals and a noise processed signal.

FIG. 10 is a figure showing experimental results of the first signal, second signal and a noise processed signal. The waveform diagram shown in the figure is given by way of illustration only and does not mean that a specific form of the present invention is limited to those shown in the figure. The collection module 110 may collect two signals and transmit to the analysis module 120. The analysis module 120 may perform feature analysis on the two signals, the features including but not limited to a waveform, a wave crest, a wave trough, peak amplitude, peak point spacing, a phase, a frequency, a period or any combination thereof. The feature results are shown in the figure, in which the first signal is a physiological signal of the living organism including a PPG signal of the living organism and a moving/vibrating signal of the living organism, and the second signal may include a moving/vibrating signal of the living organism. It can be clearly seen from the figure that the waveform, position of the wave crest, position of the wave trough, peak point spacing and phase of the first signal and the second signal are basically the same. The obvious difference between the two signals is the difference in amplitude. After the normalization process and phase adjustment, noise process may be performed on the first signal. At this moment, the second signal is taken as a reference signal, the noise process is implemented by the noise processing unit 830 in the analysis module 120, and a noise in the first signal is removed so as to obtain the noise processes signal as shown in the figure. The noise processes signal is a PPG signal of the living organism. It can be seen from the figure that the waveform of the noise processes signal is regular and flat, showing a regular distribution of the wave crests and wave troughs of the jagged wavelets in the form of a pulse waveform. The PPG signal may be outputted by the output module 140 directly as an output result, and may also be initial data or intermediate data of the subsequent step of calculating vital signs. The vital sign obtaining system may remove movement/vibration noise or interference in physiological signals of a living organism well, and the calculated amount thereof is small and the calculation result is accurate.

It should be noted that the various steps, operation processes as well as functions of each module or unit described herein may be performed according to the cases described in the present invention, and some steps or some modules or units may be omitted in a few cases. Similarly, the cases described herein is not essential to implement the advantages of the embodiments described herein, but is provided merely for the convenience of demonstration, illustration, description and illustration. For those skilled in the art, some steps may be added or deleted, some modules or units may be added or deleted, some steps may be repeated, and some modules or units may be reused based on different requirements.

It should also be understood that the structures and configurations disclosed herein are actually exemplary and are merely for the purpose of illustration and description, the specific embodiments are not to be considered in a limiting sense, and for those skilled in the art, different variations may be made according to different requirements. In addition, the subject matter disclosed herein includes various structures and configurations disclosed in the present invention, as well as all novel and non-obvious combinations and sub-combinations of other features, functions, and/or properties.

First Embodiment

The first embodiment provides a system for obtaining vital signs. An electric power 160 is turned on, the system is preset and adaptively processed, and an initial value is zeroed. A light source transmitter in the collection module 110 is lit, and two beams of light with the same wavelength are transmitted by the light source transmitter simultaneously. Types of the beams of light may include, but are not limited to, red light, green light, infrared light, blue light, violet light, yellow light, orange light, and cyan light. The two beams of light may reach skins of a living organism, and the skins may be at the same position, or may be adjacent skins near a same position. The beams of light may penetrate a skin surface layer and reach blood vessels under the skin, and two reflection signals (or refer to as reflected light) with the same wavelength are obtained after reflected by the living organism. The collection module may include two sensor receivers. The two receivers may be located at the same position or at different positions in close proximity to the living body. The two receivers may receive two reflection signals separately, and parameter states of the two receivers are different. The two receivers may be adjusted to different parameter states by adjusting parameters such as, but not limited to, resistivity, current, voltage, sensitivity of light intensity or combinations thereof. The two receivers with different parameter states may have different sensitivities to the two signals. Since a PPG signal of the living organism belongs to a low-frequency physiological signal and signal intensity thereof is relatively weak, the PPG signal of the living organism may not be received or detected when the sensitivity of the receiver is relatively low. Therefore, a first signal received by a first receiver is a physiological signal of the living organism, including a PPG signal of the living organism and a moving/vibrating signal of the living organism. A second signal received by a second receiver may include a moving/vibrating signal of the living organism. A preprocessing unit 320 of the collection module 110 may be configured to preliminarily preprocess the two collected signals, and the preprocessing may achieve an effect of smoothing the signals or removing significant interference. The preprocessing method may include, but is not limited to, low-pass filtering, bandpass filtering, wavelet transform filtering, a median filtering method, morphological filtering, a curve fitting method, or any combination thereof. The two preprocessed signals may be transmitted to an analysis module 120 directly in real-time, or may be stored in a storage device (the storage device may be an external device 150, an individual storage module in an engine 100, may be integrated in the collection module 110, may be a server 170 as well as any other engines, modules or units with a storage function) and read by the analysis module 120 later in non-real-time.

The analysis module 120 may read the two signals simultaneously, and may also read the two signals time sharing separately. After the two signals are read, feature analysis is performed on the two signals by a feature analysis unit 810 of the analysis module 120. The feature analysis may include, but is not limited to, a waveform, a wave crest, a wave trough, peak amplitude, peak point spacing, a phase, a frequency, a period, or any combination thereof. The feature results may be transmitted to the next step in real-time, or may be cached in a corresponding cache device (not shown) so as to be read by other units in non-real-time for implementing subsequent steps. After the feature analysis is performed by the feature analysis unit 810, a noise judgment step may be performed on both signals so as to judge that whether there is a noise in the first signal. If a waveform of the second signal is a straight line or the detected second signal is extraordinary weak, it can be judged that there is no noise in the first signal. If a waveform shape of the second signal is extraordinary similar to that of the first signal, and there is only a significant difference in the amplitude, it can be determined that there is a noise in the first signal. Then, the two signals are read by the normalization unit 820 in real time or non-real-time and are subjected to a normalization process. The normalization method may include, but is not limited to, min-max normalization, Z-score normalization, normalization by fractional scaling, a linear function method, a logarithmic function method, an anti-cotangent function method, a norm method, or any combination thereof. After the normalization process, an amplification factor of the two signal waveforms are adjusted to be consistent, for example, the original signals are standardized to be in the same order of magnitude and can be compared with each other, and further calculation may be performed. Further, after the normalization process, an adjustment process may be performed on the two signals, for example, but not limited to, adjusting amplitude, a phase, a frequency, intensity, or any combination thereof. The signals may be finely adjusted and processed by methods including but not limited to modulation, a carrier wave, left-right translation of waveforms, correspondence of feature points of the wave crest and wave trough, compression, frequency fine adjustment, Fourier transform, or any combination thereof. The subsequent calculation or noise process may be performed more accurately after the two signals is subjected to the adjustment process may. Then the noise processing unit 830 may perform noise process on the first signal. During the noise process, the second signal is taken as a reference signal, and a used noise processing method may include, but is not limited to, simple filtering and algorithm filtering. Specific algorithms may include, but are not limited to, simple mathematical operations such as various common addition, subtraction, multiplication, division, involution and radication; various operations of functions such as a linear function, a quadratic function, a cubic function, a quartic function, a quintic function, a power function, a compound function, a program function, a transcendental function and a complex function; various simulation calculation such as physical simulation, mathematical simulation, semi-physical simulation, continuous simulation, discrete simulation, analogue simulation, digital simulation, hybrid simulation, real-time simulation, ultra-real-time simulation and sub-real-time simulation or combination thereof. Further, a corresponding relation coefficient unit (not shown) may be used during the noise process. Different relation coefficients may be selected to perform the noise process based on a type of the light source transmitter as well as parameters such as resistivity, current, voltage and sensitivity of light intensity or any combination thereof of the sensor receiver used during the process of collecting a signal. The relation coefficient unit (not shown) may be integrated in the noise processing unit 830, may be an individual unit in the analysis module 120, may be integrated in other units, and may also be implemented by the external device 150. Further, during any process of the signal analysis or processing, the first signal and the second signal may be adjusted, for example, but not limited to, adjusting amplitude, a phase, a frequency, intensity, or any combination thereof. The method of the adjustment process may include, but is not limited to, angle modulation, phase modulation, frequency modulation, amplitude modulation, double-sideband modulation, single-sideband modulation, vestigial sideband modulation, amplitude offset modulation, phase offset modulation, quadrature amplitude modulation, frequency offset modulation, continuous phase modulation, orthogonal frequency division multiplexing, pulse code modulation, pulse width modulation, pulse amplitude modulation, pulse position modulation, pulse number modulation, trigonometric integral modulation, or any combination thereof. Accordingly, during any process of the signal analysis or process, the first signal and the second signal may be demodulated to decompose the modulated original signal. The first signal subjected to the noise process may be outputted by the output module 140 directly, or may be stored in a corresponding storage device so as to be read by the calculation module 130 in real-time or non-real-time for calculation.

The types of vital signs that may be calculated by the calculation module 130 may include, but are not limited to, one or more of vital signs such as a blood pressure, a pulse rate, blood oxygen saturation, cardiac rate variability, heart murmur, bowel sounds, a pH value, a creatinine content, a transferase content, a body temperature and a carcinoembryonic antigen content. The calculation methods may include, but are not limited to, various mathematical calculation, statistical analysis, data processing or the like. The types of data or signals related in the calculation process may include, but are not limited to, measurement of physiological parameters of a living organism, including but not limited to a height, a weight, a vital capacity, heartbeat parameters, a blood sugar content, measurement of blood viscidity, a diastolic blood pressure, a systolic blood pressure, measurement of a blood flow parameter, a PPG signal wave crest and wave trough, an ECG signal wave crest and wave trough, a pulse rate, a cardiac rate, a blood lipid content, a vascular tone, a skin tone, a brain wave frequency, gastrointestinal motility, liver and gallbladder morphology, a gastrointestinal mucosal parameter, an antibody content, an enzyme content, or any combination thereof. The calculated vital signs of the living organism may be outputted by the output module 140 in real-time or non-real-time.

Second Embodiment

The second embodiment provides a system for obtaining vital signs. An electric power 160 is turned on, the system is preset and adaptively processed, and an initial value is zeroed. A light source transmitter in the collection module 110 is lit, and two beams of light with the same wavelength are transmitted by the light source transmitter simultaneously, types of the beams of light including but not limited to, red light, green light, infrared light, blue light, violet light, yellow light, orange light, and cyan light. The two beams of light may reach skins of the living organism separately, and the skins may be at the same position, or may be adjacent skins near a same position. The beams of light may penetrate a skin surface layer and reach blood vessels under the skin, and two reflection signals (or refer to as reflected light) with the same wavelength are obtained after reflected by the living organism. The collection module may include one sensor receiver, and the receiver may adjust parameter states so as to receive two reflection signals time sharing. The adjustable parameters may include, but are not limited to, resistivity, current, voltage, sensitivity of light intensity, or any combination thereof. The receivers may have different signal sensitivities when the parameter states are different. Since a PPG signal of the living organism belongs to a low-frequency physiological signal and signal intensity thereof is relatively weak, the PPG signal of the living organism may not be received or detected when the sensitivity of the receiver is relatively low. Therefore, the receiver may receive two different signals time sharing, in which a first signal is a physiological signal of the living organism including a PPG signal of the living organism and a moving/vibrating signal of the living organism, and a second signal may include a moving/vibrating signal of the living organism. A preprocessing unit 320 of the collection module 110 may be configured to preliminarily preprocess the two collected signals, and the preprocessing may achieve an effect of smoothing the signals or removing significant interference. The preprocessing method may include, but is not limited to, low-pass filtering, bandpass filtering, wavelet transform filtering, a median filtering method, morphological filtering and a curve fitting method. The two preprocessed signals may be transmitted to an analysis module 120 directly in real-time, or may be stored in a storage device (the storage device may be an external device 150, an individual storage module in an engine 100, may be integrated in the collection module 110, may be a server 170 as well as any other engines, modules or units with a storage function) and read by the analysis module 120 later in non-real-time.

The subsequent operational processes and control steps of the analysis module 120, calculation module 130 as well as output module 140 are the same as those in the first embodiment.

Third Embodiment

The third embodiment provides a system for obtaining vital signs. An electric power 160 is turned on, the system is preset and adaptively processed, and an initial value is zeroed. A light source transmitter in the collection module 110 is lit, and two beams of light with different wavelengths are transmitted by the transmitter simultaneously, types of the beams of light including but not limited to, red light, green light, infrared light, blue light, violet light, yellow light, orange light, and cyan light. The two beams of light may reach skins of the living organism separately, and the skins may be at the same position, or may be adjacent skins near a same position. Since penetrating capacities of the two beams of light are different, a first beam of light may penetrate a skin surface layer of the living organism and reach blood vessels under the skin, and a first reflection signal (or refer to as first reflected light) is obtained after reflected by the living organism. A second beam of light with relatively weak penetrating capacity may not penetrate the skin surface layer and reach depth of the skin, and therefore a second reflection signal (or refer to as second reflected light) is obtained after reflected on the skin surface layer of the living organism. The collection module 110 may include two sensor receivers and the two receivers may be located at the same position or at different positions in close proximity to the living body. Parameters of the two receivers such as resistivity, current, voltage and sensitivity of light intensity are all the same. The two receivers may receive two reflection signals separately, and a first signal received by a first receiver is a physiological signal of the living organism, including a PPG signal of the living organism and a moving/vibrating signal of the living organism. A second signal received by a second receiver may include a moving/vibrating signal of the living organism. A preprocessing unit 320 of the collection module 110 may be configured to preliminarily preprocess the two collected signals, and the preprocessing may achieve an effect of smoothing the signals or removing significant interference. The preprocessing method may include, but is not limited to, low-pass filtering, bandpass filtering, wavelet transform filtering, a median filtering method, morphological filtering, a curve fitting method, or any combination thereof. The two preprocessed signals may be transmitted to an analysis module 120 directly in real-time, or may be stored in a storage device (the storage device may be an external device 150, an individual storage module in an engine 100, may be integrated in the collection module 110, may be a server 170 as well as any other engines, modules or units with a storage function) and read by the analysis module 120 later in non-real-time.

The subsequent operational processes and control steps of the analysis module 120, calculation module 130 as well as output module 140 are the same as those in the first embodiment.

Fourth Embodiment

The fourth embodiment provides a system for obtaining vital signs. An electric power 160 is turned on, the system is preset and adaptively processed, and an initial value is zeroed. A light source transmitter in a collection module 110 is lit, and two beams of light with different wavelengths are transmitted by the transmitter simultaneously. Types of the beams of light may include, but are not limited to, red light, green light, infrared light, blue light, violet light, yellow light, orange light, and cyan light. The two beams of light may reach skins of a living organism separately, and the skins may be at the same position, or may be adjacent skins near a same position. Since penetrating capacities of the two beams of light are different, a first beam of light may penetrate a skin surface layer of the living organism and reach blood vessels under the skin, and a first reflection signal (or refer to as first reflected light) is obtained after reflected by the living organism. A second beam of light with relatively weak penetrating capacity may not penetrate the skin surface layer and reach depth of the skin, and therefore a second reflection signal (or refer to as second reflected light) is obtained after reflected on the skin surface layer of the living organism. The collection module 110 may include one sensor receiver, and the receiver may receive two reflection signals time sharing. A first signal is reflected by blood vessels under the skin of the living organism, and may include a PPG signal and a moving/vibrating signal of the living organism. A second signal is reflected by the skin surface layer of the living organism, and may include a moving/vibrating signal of the living organism. A preprocessing unit 320 of the collection module 110 may be configured to preliminarily preprocess the two collected signals, and the preprocessing may achieve an effect of smoothing the signals or removing significant interference. The preprocessing method may include, but is not limited to, low-pass filtering, bandpass filtering, wavelet transform filtering, a median filtering method, morphological filtering, a curve fitting method, or any combination thereof. The two preprocessed signals may be transmitted to an analysis module 120 directly in real-time, or may be stored in a storage device (the storage device may be an external device 150, an individual storage module in an engine 100, may be integrated in the collection module 110, may be a server 170 as well as any other engines, modules or units with a storage function) and read by the analysis module 120 later in non-real-time.

The subsequent operational processes and control steps of the analysis module 120, calculation module 130 as well as output module 140 are the same as those in the first embodiment.

Fifth Embodiment

The fifth embodiment provides a system for obtaining vital signs. An electric power 160 is turned on, the system is preset and adaptively processed, and an initial value is zeroed. A plurality of light source transmitters in a collection module 110 are lit, and a plurality of beams of light with different features are transmitted by the plurality of light source transmitters time sharing. The plurality of beams of light may be obtained by adding the same or different carrier signals to one or more original beams of light/signals and performing modulation. The spectral bands to which the original beams of light/signals belong may include, but are not limited to, a visible spectrum, an infrared spectrum and a far-infrared spectrum. The plurality of beams of light may be completely different from each other, or every two of them may be the same, or they may be combined in any form into two or more groups of identical or different beams of light. The modulation process in which carrier signals are added may include, but is not limited to, angle modulation, phase modulation, frequency modulation, amplitude modulation, double-sideband modulation, single-sideband modulation, vestigial sideband modulation, amplitude offset modulation, phase offset modulation, quadrature amplitude modulation, frequency offset modulation, continuous phase modulation, orthogonal frequency division multiplexing, pulse code modulation, pulse width modulation, pulse amplitude modulation, pulse position modulation, pulse number modulation, trigonometric integral modulation, or any combination thereof. The plurality of beams of light may be transmitted to skins of a living organism, and the skins may be at the same position of the living organism, or may be adjacent skins near a same position, or different positions of the living organism. The plurality of beams of light may have different penetrating capacities, and the capacity to penetrate the skin surface layer of the living organism is also different. Therefore, a plurality of different reflection signals may be obtained after the plurality of beams of light reach the living organism and are reflected by the living organism. The reflection signals may reflect different physiological or psychological parameters of the living organism, such as but not limited to blood flow at different locations, movement/vibration of the skin surface layer at different locations, an organ state, heartbeat parameters, pulse beat parameters, skin surface tension, skin elasticity, a bone state, a muscle state, a body fat content, or any combination thereof. The collection module 110 may include a plurality of sensor receivers, and the receivers may receive a plurality of reflection signals simultaneously or time sharing. A preprocessing unit 320 of the collection module 110 may be configured to preliminarily preprocess the plurality of collected signals, and the preprocessing may achieve an effect of smoothing the signals or removing significant interference. The preprocessing method may include, but is not limited to, low-pass filtering, bandpass filtering, wavelet transform filtering, a median filtering method, morphological filtering, a curve fitting method, or any combination thereof. The plurality preprocessed signals may be transmitted to an analysis module 120 directly in real-time, or may be stored in a storage device (the storage device may be an external device 150, an individual storage module in an engine 100, may be integrated in the collection module 110, may be a server 170 as well as any other engines, modules or units with a storage function) and read by the analysis module 120 later in non-real-time.

The subsequent operational processes and control steps of the analysis module 120, calculation module 130 as well as output module 140 are the same as those in the first embodiment.

We claim:

1. A system for monitoring a physiological signal of a subject, comprising:
    a computer-readable storage medium storing a set of instructions for processing data;
    at least one processor in communication with the computer-readable storage medium, wherein when executing the set of instructions, the at least one processor is directed to:
        direct a transmitter to transmit a beam of light to the subject;
        receive a first signal collected by a first receiver according to a first receiving parameter of the first receiver, the first signal being reflected by the subject in response to the beam of light and at least comprising a photoplethysmograph (PPG) signal relating to the subject and a moving/vibrating signal relating to the subject, wherein the first receiving parameter is used to set a first sensitivity of light intensity of the first receiver and includes at least one of a first resistance, a first current, or a first voltage;

receive a second signal collected by a second receiver according to a second receiving parameter of the second receiver, the second signal being reflected by the subject in response to the beam of light and at least comprising the moving/vibrating signal relating to the subject, wherein the second receiving parameter is used to set a second sensitivity of light intensity of the second receiver and includes at least one of a second resistance, a second current, or a second voltage, wherein the first receiving parameter of the first receiver is different from the second receiving parameter of the second receiver; and the first sensitivity of light intensity of the first receiver is different from the second sensitivity of light intensity of the second receiver;

set a correlation coefficient based on the first receiving parameter of the first receiver or the second receiving parameter of the second receiver;

identify, according to a signal processing technique, the PPG signal of the subject in the first signal by removing the moving/vibrating signal from the first signal based on the second signal and the correlation coefficient;

monitor a physiological signal of the subject based on the PPG signal; and transmit, via a network, a monitoring result to a third party associated with the subject, the third party including at least one of a hospital, a nursing facility, or a member associated with the subject.

2. The system of claim 1, wherein a spectrum of the beam of light includes at least one of a visible light spectrum, an infrared light spectrum, or a far infrared light spectrum.

3. The system of claim 1, wherein to identify, according to the signal processing technique, the PPG signal of the subject in the first signal by removing the moving/vibrating signal from the first signal based on the second signal and the correlation coefficient, the at least one processor is further directed to:

perform a normalization on the first signal and the second signal; and identify, according to the signal processing technique, the PPG signal of the subject in the first signal by removing the moving/vibrating signal from a normalized first signal based on a normalized second signal.

4. The system of claim 1, wherein the correlation coefficient is associated with a type of the transmitter.

5. The system of claim 1, wherein the at least one processor is further directed to:

output the physiological signal of the subject to a displaying device.

6. The system of claim 5, wherein the at least one processor is further directed to:

instruct the displaying device to display the physiological signal of the subject in a digital form, a waveform form, an analog waveform form, a symbol form, a code form, a voice form, a video form, or an image form.

7. A method for monitoring a physiological signal of a subject implemented on a computing device having at least one processor, at least one computer-readable storage medium, and a communication platform connected to a network, the method comprising:

directing a transmitter to transmit a beam of light to the subject;

receiving a first signal collected by a first receiver according to a first receiving parameter of the first receiver, the first signal being reflected by the subject in response to the beam of light and at least comprising a photoplethysmograph (PPG) signal relating to the subject and a moving/vibrating signal relating to the subject, wherein the first receiving parameter is used to set a first sensitivity of light intensity of the first receiver and includes at least one of a first resistance, a first current, or a first voltage;

receiving a second signal collected by a second receiver according to a second receiving parameter of the second receiver, the second signal being reflected by the subject in response to the beam of light and at least comprising the moving/vibrating signal relating to the subject, wherein the second receiving parameter is used to set a second sensitivity of light intensity of the second receiver and includes at least one of a second resistance, a second current, or a second voltage, wherein the first receiving parameter of the first receiver is different from the second receiving parameter of the second receiver; and the first sensitivity of light intensity of the first receiver is different from the second sensitivity of light intensity of the second receiver;

setting a correlation coefficient based on the first receiving parameter of the first receiver or the second receiving parameter of the second receiver;

identifying, according to a signal processing technique, the PPG signal of the subject in the first signal by removing the moving/vibrating signal from the first signal based on the second signal and the correlation coefficient;

monitoring a physiological signal of the subject based on the PPG signal; and transmitting, via the network, a monitoring result to a third party associated with the subject, the third party including at least one of a hospital, a nursing facility, or a member associated with the subject.

8. The method of claim 7, wherein a spectrum of the beam of light includes at least one of a visible light spectrum, an infrared light spectrum, or a far infrared light spectrum.

9. The method of claim 7, wherein the identifying, according to the signal processing technique, the PPG signal of the subject in the first signal by removing the moving/vibrating signal from the first signal based on the second signal and the correlation coefficient includes:

performing a normalization on the first signal and the second signal; and identifying, according to the signal processing technique, the PPG signal of the subject in the first signal by removing the moving/vibrating signal from a normalized first signal based on a normalized second signal.

10. The method of claim 7, wherein the correlation coefficient is associated with a type of the transmitter.

11. The method of claim 7, wherein the method further includes:

outputting the physiological signal of the subject to a displaying device.

12. The method of claim 7, wherein the method further includes:

instructing the displaying device to display the physiological signal of the subject in a digital form, a waveform form, an analog waveform form, a symbol form, a code form, a voice form, a video form, or an image form.

13. A non-transitory computer readable medium comprising a set of instructions, wherein when executed by at least one processor, the set of instructions cause the at least one processor to effectuate a method comprising:
- directing a transmitter to transmit a beam of light to a subject;
- receiving a first signal collected by a first receiver according to a first receiving parameter of the first receiver, the first signal being reflected by the subject in response to the beam of light and at least comprising a photoplethysmograph (PPG) signal relating to the subject and a moving/vibrating signal relating to the subject, wherein the first receiving parameter is used to set a first sensitivity of light intensity of the first receiver and includes at least one of a first resistance, a first current, or a first voltage;
- receiving a second signal collected by a second receiver according to a second receiving parameter of the second receiver, the second signal being reflected by the subject in response to the beam of light and at least comprising the moving/vibrating signal relating to the subject, wherein the second receiving parameter is used to set a second sensitivity of light intensity of the second receiver and includes at least one of a second resistance, a second current, or a second voltage, wherein
  - the first receiving parameter of the first receiver is different from the second receiving parameter of the second receiver; and
  - the first sensitivity of light intensity of the first receiver is different from the second sensitivity of light intensity of the second receiver;
- setting a correlation coefficient based on the first receiving parameter of the first receiver or the second receiving parameter of the second receiver;
- identifying, according to a signal processing technique, the PPG signal of the subject in the first signal by removing the moving/vibrating signal from the first signal based on the second signal and the correlation coefficient;
- monitoring a physiological signal of the subject based on the PPG signal; and
- transmitting, via a network, a monitoring result to a third party associated with the subject, the third party including at least one of a hospital, a nursing facility, or a member associated with the subject.

14. The non-transitory computer readable medium of claim 13, wherein a spectrum of the beam of light includes at least one of a visible light spectrum, an infrared light spectrum, or a far infrared light spectrum.

15. The non-transitory computer readable medium of claim 13, wherein the identifying, according to the signal processing technique, the PPG signal of the subject in the first signal by removing the moving/vibrating signal from the first signal based on the second signal and the correlation coefficient, includes:
- performing a normalization on the first signal and the second signal; and
- identifying, according to the signal processing technique, the PPG signal of the subject in the first signal by removing the moving/vibrating signal from a normalized first signal based on a normalized second signal.

16. The non-transitory computer readable medium of claim 13, wherein the correlation coefficient is associated with a type of the transmitter.

17. The non-transitory computer readable medium of claim 13, wherein when executed by the at least one processor, the set of instructions cause the at least one processor to effectuate the method further comprising:
- outputting the physiological signal of the subject to a displaying device.

18. The non-transitory computer readable medium of claim 13, wherein when executed by the at least one processor, the set of instructions cause the at least one processor to effectuate the method further comprising:
- instructing the displaying device to display the physiological signal of the subject in a digital form, a waveform form, an analog waveform form, a symbol form, a code form, a voice form, a video form, or an image form.

* * * * *